(12) United States Patent
Coe et al.

(10) Patent No.: US 7,144,908 B2
(45) Date of Patent: Dec. 5, 2006

(54) AGONISTS OF BETA-ADRENOCEPTORS

(75) Inventors: Diane Mary Coe, Stevenage (GB); Michael John Monteith, Dartford (GB); Panayiotis Alexandrou Procopiou, Stevenage (GB)

(73) Assignee: Glaxo Group Limited, Greenford (GB)

( * ) Notice: Subject to any disclaimer, the term of this patent is extended or adjusted under 35 U.S.C. 154(b) by 90 days.

(21) Appl. No.: 10/471,201

(22) PCT Filed: Mar. 4, 2002

(86) PCT No.: PCT/EP02/02317

§ 371 (c)(1), (2), (4) Date: Mar. 5, 2004

(87) PCT Pub. No.: WO02/070490

PCT Pub. Date: Sep. 12, 2002

(65) Prior Publication Data

US 2004/0242890 A1  Dec. 2, 2004

(51) Int. Cl.
- A61K 31/466 (2006.01)
- A61K 31/4245 (2006.01)
- A61K 31/4196 (2006.01)
- C07D 233/86 (2006.01)
- C07D 271/07 (2006.01)
- C07D 249/12 (2006.01)

(52) U.S. Cl. .............. 514/391; 514/364; 514/384; 548/321.1; 548/132; 548/263.2

(58) Field of Classification Search ............... 560/108; 514/396, 406, 391, 364, 384; 548/377.1, 548/335.1, 321.1, 132, 263.2
See application file for complete search history.

(56) References Cited

U.S. PATENT DOCUMENTS 4,990,505 A * 2/1991 Skidmore et al. ...... 514/211.01
4,992,474 A * 2/1991 Skidmore et al. ........... 514/653

FOREIGN PATENT DOCUMENTS

| | | |
|---|---|---|
| EP | 0 162 576 | 11/1985 |
| EP | 0 220 054 | 4/1987 |
| EP | 0 220 878 | 5/1987 |
| EP | 0 223 410 | 5/1987 |
| EP | 0 286 242 | 10/1988 |
| EP | 0 303 465 | 2/1989 |
| EP | 0 317 206 | 5/1989 |
| EP | 0 416 951 | 3/1991 |
| GB | 2140800 | 12/1984 |
| GB | 2 159 151 | 11/1985 |
| GB | 2 162 842 | 2/1986 |
| WO | 95/01170 | 1/1995 |

* cited by examiner

Primary Examiner—Kamal A. Saeed
Assistant Examiner—Michael P. Barker
(74) Attorney, Agent, or Firm—Robert J. Smith

(57) ABSTRACT

The present invention relates to novel compounds of formula (I), to a process for their manufacture, to pharmaceutical compositions containing them, and to their use in therapy, in particular their use in the prophylaxis and treatment of respiratory diseases.

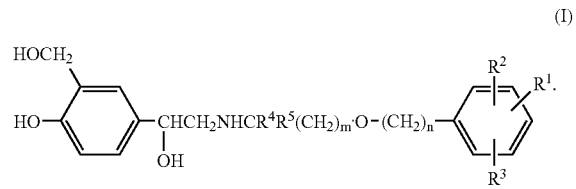

20 Claims, No Drawings

AGONISTS OF BETA-ADRENOCEPTORS

This application is filed under 35 U.S.C. § 371 as the U.S. National Phase Application of International Application No. PCT/EP02/02317 filed Mar. 4, 2002 claiming priority from Great Britain Application Nos. 0105740.5 and 0126994.3 filed Mar. 8, 2001 and Nov. 9, 2001, the disclosures of which are incorporated herein by reference in their entirety.

The present invention is concerned with phenethanolamine derivatives, processes for their preparation, compositions containing them and their use in medicine, particularly in the prophylaxis and treatment of respiratory diseases.

Certain phenethanolamine compounds are known in the art as having selective stimulant action at $\beta_2$-adrenoreceptors and therefore having utility in the treatment of bronchial asthma and related disorders. Thus GB 2 140 800 describes phenethanolamine compounds including 4-hydroxy-a$^1$-[[[6-(4phenylbutoxy)hexyl]amino]methyl]-1,3-benzenedimethanol 1-hydroxy-2-naphthalenecarboxylate (salmeterol xinafoate) which is now used clinically in the treatment of such medical conditions.

Although salmeterol and the other commercially available $\beta_2$-adrenoreceptor agonists are effective bronchodilators, the maximum duration of action is 12 hours, hence twice daily dosing is often required. There is therefore a clinical need for compounds having potent and selective stimulant action at $\beta_2$-adrenoreceptors and having an advantageous profile of action.

According to the present invention, there is provided a compound of formula (I)

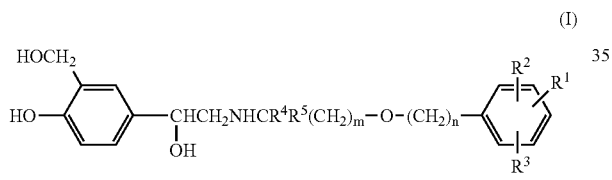

(I)

or a salt, solvate, or physiologically functional derivative thereof, wherein:

m is an integer of from 2 to 8;
n is an integer of from 3 to 11, preferably from 3 to 7;
with the proviso that m+n is 5 to 19, preferably 5 to 12;
$R^1$ is —X—$R^6$; wherein
X is selected from —(CH$_2$)$_p$— and C$_{2-6}$alkenylene;
$R^6$ is selected from

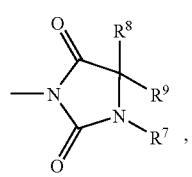

(a)

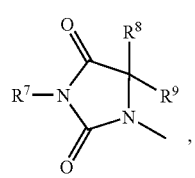

(b)

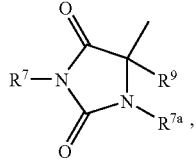

(c)

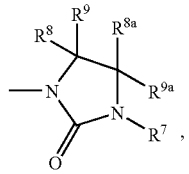

(d)

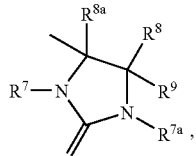

(e)

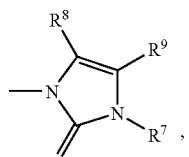

(f)

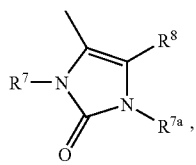

(g)

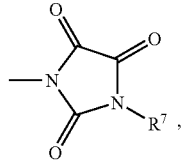

(h)

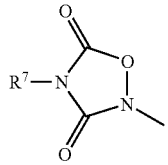

(i)

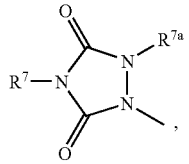

(j)

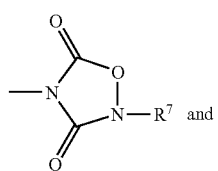

(k)

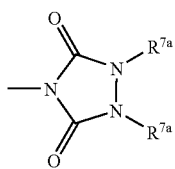

(l)

$R^7$ and $R^{7a}$ are independently selected from hydrogen, $C_{1-6}$alkyl, $C_{3-7}$cycloalkyl, $C(O)R^{7b}$, $C(O)NHR^{7b}$, phenyl, naphthyl, hetaryl, and phenyl($C_{1-4}$alkyl)-, and $R^7$ and $R^{7a}$ are optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$alkyl), —SO$_2$(phenyl), —CO$_2$H, and —CO$_2$($C_{1-4}$alkyl);

$R^{7b}$ is selected from hydrogen, $C_{1-6}$alkyl, $C_{3-7}$cycloalkyl, phenyl, naphthyl, hetaryl, and phenyl($C_{1-4}$alkyl), and $R^{7b}$ is optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$alkyl), —SO$_2$(phenyl), —CO$_2$H, and —CO$_2$($C_{1-4}$alkyl);

$R^8$, $R^{8a}$, $R^9$ and $R^{9a}$ are independently selected from hydrogen, $C_{1-6}$alkyl, $C_{3-7}$cycloalkyl, phenyl, naphthyl, hetaryl, phenyl($C_{1-4}$alkyl)-, —NR$^{10a}$SO$_2$R$^{10}$, —NR$^{10a}$C(O)NR$^{10}$R$^{11}$, —SO$_2$NR$^{10}$R$^{11}$, and $C_{1-6}$alkyl substituted by —CO$^2$R$^{10}$ or —C(O)NR$^{10}$, R$^{11}$;

$R^{10}$, $R^{10a}$ and $R^{11}$ are independently selected from hydrogen, $C_{1-6}$alkyl, $C_{3-6}$cycloalkyl, phenyl, and phenyl ($C_{1-4}$ alkyl)-;

p is an integer from 0 to 6, preferably from 0 to 4:

$R^2$ is selected from hydrogen, $C_{1-6}$alkyl, $C_{1-6}$alkoxy, phenyl, halo, and $C_{1-6}$haloalkyl;

$R^3$ is selected from hydrogen, hydroxyl, $C_{1-6}$alkyl, $C_{1-6}$alkoxy, phenyl, halo, $C_{1-6}$haloalkyl, —NR$^7$CONR$^7$R$^{7a}$ and —SO$_2$NR$^a$R$^b$;

wherein R$^a$ and R$^b$ are independently selected from hydrogen, $C_{1-6}$alkyl, $C_{3-6}$cycloalkyl, phenyl, and phenyl ($C_{1-4}$ alkyl), or R$^a$ and R$^b$, together with the nitrogen to which they are bonded, form a 5-, 6-, or 7-membered nitrogen containing ring;

and R$^a$ and R$^b$ are each optionally substituted by one or two groups selected from halo, $C_{1-6}$alkyl, and $C_{1-6}$haloalkyl; and $R^4$ and $R^5$ are independently selected from hydrogen and $C_{1-4}$alkyl with the proviso that the total number of carbon atoms in $R^4$ and $R^5$ is not more than 4.

In the definition of X, the term alkenylene includes both cis and trans structures. Examples of suitable alkenylene groups include —CH=CH—.

In the definition of $R^3$, where R$^a$ and R$^b$ together with the nitrogen atom to which they are bonded form a 5-, 6- or 7-membered nitrogen containing ring the term "5-, 6-, or 7-membered nitrogen containing ring" means a 5-, 6-, or 7-membered saturated or unsaturated ring which includes the sulphonamide nitrogen atom and optionally 1 or 2 other heteroatoms independently selected from nitrogen, sulphur, and oxygen. Suitable examples of such a ring include piperidinyl, morpholinyl, and piperazinyl.

In the definition of $R^7$, the term "hetaryl" means a 5- or 6-membered heteroaromatic ring, such as thienyl, pyridyl or imidazolyl.

In the compounds of formula (I) $R^2$ and $R^3$ preferably each represent hydrogen.

In the compounds of formula (I), $R^4$ and $R^5$ are preferably independently selected from hydrogen and methyl, more preferably $R^4$ and $R^5$ are both hydrogen.

In the compounds of formula (I), m is suitably 3, 4, 5 or 6 and n is suitably 3, 4, 5 or 6. Preferably m is 5 and preferably n is 4 or 5, such that m+n is 8, 9 or 10, preferably 9.

According to a preferred aspect of the invention, there is provided a compound of formula (Ia)

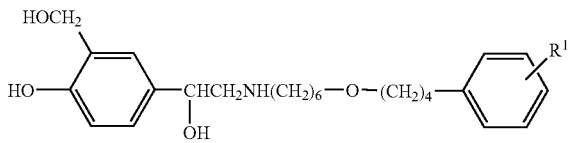

(Ia)

or a salt, solvate, or physiologically functional derivative thereof, wherein $R^1$ is as defined above for formula (I).

According to a further preferred aspect of the invention, there is provided a compound of formula (Ib)

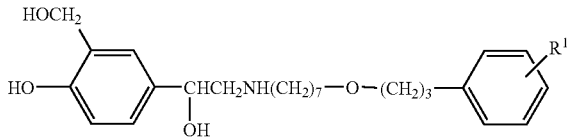

(Ib)

or a salt, solvate, or physiologically functional derivative thereof, wherein $R^1$ is as defined above for formula (I).

According to a yet further preferred aspect of the invention, there is provided a compound or formula (Ic):

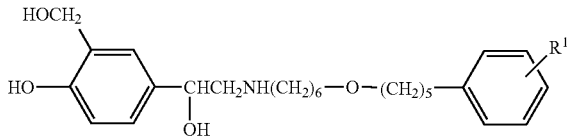

(Ic)

or a salt, solvate, or physiologically functional derivative thereof, wherein $R^1$ is a defined above for formula (I).

Compounds or formulae (Ia) and (Ic) are particularly preferred.

In the compounds of formulae (I), (Ia), (Ib) and (Ic) the group $R^1$ is preferably attached to the meta-position relative to the —O—(CH$_2$)$_n$—, —O—(CH$_2$)$_4$—, —O—(CH$_2$)$_3$— or —O—(CH$_2$)$_5$ link respectively.

In the compounds of formulae (I), (Ia), (Ib) and (Ic) the group $R^6$ is preferably linked to the moiety X or directly to the phenyl ring via one of the ring nitrogen atoms of the group $R^6$. Advantageously the group $R^6$ is selected from the groups (a), (b), (d) and (f).

In the compounds of formulae (I), (Ia), (Ib) and (Ic), $R^7$, $R^{7a}$, $R^8$, $R^{8a}$, $R^9$ and $R^{9a}$ are preferably all hydrogen.

Particularly preferred are compounds wherein $R^6$ is selected from the groups (a), (b), (d) and (f) and $R^7$, $R^{7a}$, $R^8$ and $R^9$ are all hydrogen.

Also particularly preferred are compounds wherein $R^6$ is a group (a) and $R^8$ represents —NHCONH$_2$ and compounds wherein $R^6$ is a group (b) and $R^7$ represents —CH$_2$CONH$_2$.

It is to be understood that the present invention covers all combinations of particular and preferred groups described hereinabove.

The compounds of formulae (I), (Ia), (Ib) and (Ic) include an asymmetric centre, namely the carbon atom of the

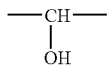

group. The present invention includes both (S) and (R) enantiomers either in substantially pure form or admixed in any proportions. Preferably, the compounds of the invention are in the form of the (R) enantiomers.

Similarly, where $R^4$ and $R^5$ are different groups, the carbon atom to which they are attached is an asymmetric centre and the present invention includes both (S) and (R) enantiomers at this centre either in substantially pure form or admixed in any proportions.

Thus the compounds of formulae (I), (Ia), (Ib) and (Ic) include all enantiomers and diastereoisomers as well as mixtures thereof in any proportions.

Preferred compounds of the invention include:
3-[3-(4-{[6-([2-hydroxy-2-[4-hydroxy-3-(hydroxymethyl) phenyl]ethyl}-amino)hexyl]oxy}butyl)phenyl]imidazolidine-2,4-dione;
3-[3-(3-{[7-({2-hydroxy-2-[4-hydroxy-3-(hydroxymethyl) phenyl]ethyl}-amino)heptyl]oxy}propyl)phenyl]imidazolidine-2,4-dione;
1-[3-(4-{[6-({2-Hydroxy-2-[4-hydroxy-3-(hydroxymethyl) phenyl]ethyl]amino)hexyl]oxy}butyl)phenyl]imidazolidine-2-one;
1-[3-(4-{[6-({2-hydroxy-2-[4-hydroxy-3-(hydroxymethyl) phenyl]ethyl}-amino)hexyl]oxy}butyl)phenyl]imidazolidine-2,4-dione;
3-[3-(4-{[6-([(2R)-2-hydroxy-2-[4-hydroxy-3-(hydroxymethyl)phenyl]ethyl}amino)hexyl]oxy}butyl)phenyl]imidazolidine-2,4-dione;
3-[3-(4-{[6-([(2R)-2-hydroxy-2-[4-hydroxy-3-(hydroxymethyl)phenyl]ethyl}amino)hexyl]oxy}butyl)phenyl]imidazolidine-2,4-dione;
3-[3-(4-{[6-([(2R)-2-hydroxy-2-[4-hydroxy-3-(hydroxymethyl)phenyl]ethyl}amino)hexyl]oxy}butyl)phenyl]imidazolidine-2,4-dione;
3-[3-(4-{[6-({(2S)-2-hydroxy-2-[4-hydroxy-3-(hydroxymethyl)phenyl]ethyl}amino)hexyl]oxy}butyl)phenyl]imidazolidine-2,4-dione;
3-[4-(4-{[6-({(2R)-2-hydroxy-2-[4-hydroxy-3-(hydroxymethyl)phenyl]ethyl}amino)hexyl]oxy}butyl)phenyl]imidazolidine-2,4-dione;
3-[2-(4-{[6-({(2R)-2-hydroxy-2-[4-hydroxy-3-(hydroxymethyl)phenyl]ethyl}amino)hexyl]oxy}butyl)phenyl]imidazolidine-2,4-dione;
3-[3-(4-{[6-({(2R)-2-hydroxy-2-[4-hydroxy-3-(hydroxymethyl)phenyl]ethyl}amino)hexyl]oxy}butyl)benzyl]imidazolidine-2,4-dione;
3-[3-(5-{[5-({(2R)-2-hydroxy-2-[4-hydroxy-3-(hydroxymethyl)phenyl]ethyl}amino)pentyl]oxy}pentyl)phenyl] imidazolidine-2,4-dione;
3-[3-(5-{[6-({(2R)-2-hydroxy-2-[4-hydroxy-3-(hydroxymethyl)phenyl]ethyl}amino)hexyl]oxy}pentyl)phenyl]imidazolidine-2,4-dione;
3-[3-(6-{[6-({(2R)-2-hydroxy-2-[4-hydroxy-3-(hydroxymethyl)phenyl]ethyl}amino)hexyl]oxy}hexyl)phenyl]imidazolidine-2,4-dione;
(5R)-5-[3-(4-{[6-({(2R)-2-hydroxy-2-[4-hydroxy-3-(hydroxymethyl)phenyl]ethyl}amino)hexyl]oxy}butyl)benzyl]-5-methylimidazolidine-2,4-dione;
(5S)-5-[3-(4-{[6-({(2R)-2-hydroxy-2-[4-hydroxy-3-(hydroxymethyl)phenyl]ethyl}amino)hexyl]oxy}butyl)benzyl]-5-methylimidazolidine-2,4-dione;
2-{3-[3-(4-{[6-({(2R)-2-hydroxy-2-[4-hydroxy-3-(hydroxymethyl)phenyl]ethyl}amino)hexyl]oxy}butyl)phenyl]-2,4-dioxoimidazolidin-1-yl}acetamide;
5-[4-(4-{[6-({(2R)-2-hydroxy-2-[4-hydroxy-3-(hydroxymethyl)phenyl]ethyl}amino)hexyl]oxy}butyl)benzyl]imidazolidine-2,4-dione;
1-[3-(4-{[6-({(2R)-2-hydroxy-2-[4-hydroxy-3-(hydroxymethyl)phenyl]ethyl}amino)hexyl]oxy}butyl)phenyl]-1,3-dihydro-2H-imidazol 1-2-one;
3-[3-(4-{[6-({(2R)-2-hydroxy-2-[4-hydroxy-3-(hydroxymethyl)phenyl]ethyl}amino)hexyl]oxy}butyl)phenyl]-5,5-dimethylimidazolidine-2,4-dione;
3-[3-(3-{[7-({(2R)-2-hydroxy-2-[4-hydroxy-3-(hydroxymethyl)phenyl]ethyl}amino)heptyl]oxy}propyl)phenyl]-1-(methylsulfonyl)imidazolidine-2,4-dione;
1-[3-(3-{[6-({(2R)-2-hydroxy-2-[4-hydroxy-3-(hydroxymethyl)phenyl]ethyl}amino)hexyl]oxy}propyl)phenyl]imidazolidine-2,4-dione;
N-{1-[3-(4-{[6-({(2R)-2-hydroxy-2-[4-hydroxy-3-(hydroxymethyl)phenyl]ethyl}amino)hexyl]oxy}butyl)benzyl]-2,5-dioxoimidazolidin-4-yl}urea;
3-benzyl-1-[3-(4-{[6-({(2R)-2-hydroxy-2-[4-hydroxy-3-(hydroxymethyl)phenyl]ethyl}amino)hexyl]oxy}butyl) phenyl]imidazolidine-2,4-dione;
1-[3-(4-{[6-({(2R)-2-hydroxy-2-[4-hydroxy-3-(hydroxymethyl)phenyl]ethyl}amino)hexyl]oxy}butyl)phenyl]-3-methylimidazolidine-2,4-dione;
{3-[3-(4-{[6-({(2R)-2-hydroxy-2-[4-hydroxy-3-(hydroxymethyl)phenyl]ethyl}amino)hexyl]oxy}butyl)phenyl]-2,5-dioxoimidazolidin-1-yl};
2-{3-[3-(4-{[6-({(2R)-2-hydroxy-2-[4-hydroxy-3-(hydroxymethyl)phenyl]ethyl}amino)hexyl]oxy}butyl)phenyl]-2,5-dioxoimidazolidin-1-yl}acetamide;
1-[3-(4-{[6-({(2R)-2-hydroxy-2-[4-hydroxy-3-(hydroxymethyl)phenyl]ethyl}amino)hexyl]oxy}butyl)benzyl]imidazolidine-2,4-dione;
1-Benzyl-3-[3-(4-{[6-({(2R)-2-hydroxy-2-[4-hydroxy-3-(hydroxymethyl)phenyl]ethyl}amino)hexyl]oxy}butyl) phenyl]imidazolidine-2,4-dione;
3-[3-(4-{[6-({(2R)-2-Hydroxy-2-[4-hydroxy-3-(hydroxymethyl)phenyl]ethyl}amino)hexyl]oxy}butyl)phenyl]-1-(methylsulfonyl)imidazolidine-2,4-dione; and
4-[3-(4-{[6-({(2R)-2-hydroxy-2-[4-hydroxy-3-(hydroxymethyl)phenyl]ethyl}amino)hexyl]oxy}butyl)phenyl]-1,2,4-triazolidine-3,5-dione;

and salts, solvates, and physiologically functional derivatives thereof.

Particularly preferred compounds of the invention include:
3-[3-(4-{[6-([(2R)-2-hydroxy-2-[4-hydroxy-3-(hydroxymethyl)phenyl]ethyl}-amino)hexyl]oxy}butyl)phenyl]imidazolidine-2,4-dione;
3-[3-(4-{[6-([(2S)-2-hydroxy-2-[4-hydroxy-3-(hydroxymethyl)phenyl]ethyl}-amino)hexyl]oxy}butyl)phenyl]imidazolidine-2,4-dione;
3-[3-(4-{[6-([(2R/S)-2-hydroxy-2-[4-hydroxy-3-(hydroxymethyl)phenyl]ethyl}-amino)hexyl]oxy}butyl)phenyl]imidazolidine-2,4-dione;

2-{3-[3-(4-{[6-({(2R)-2-hydroxy-2-[4-hydroxy-3-(hydroxymethyl)phenyl]ethyl}amino)hexyl]oxy}butyl)phenyl]-2,5-dioxoimidazolidin-1-yl}acetamide acetate;

N-{1-[3-(4-{[6-({(2R)-2-hydroxy-2-[4-hydroxy-3-(hydroxymethyl)phenyl]ethyl}amino)hexyl]oxy}butyl)benzyl]-2,5-dioxoimidazolidin-4-yl}urea acetate;

3-[3-(5-{[6-({(2R)-2-hydroxy-2-[4-hydroxy-3-(hydroxymethyl)phenyl]ethyl}amino)hexyl]oxy}pentyl)phenyl]imidazolidine-2,4-dione acetate;

and salts, solvates, and physiologically functional derivatives thereof.

Especially preferred is 3-[3-(4-{[6-([(2R)-2-hydroxy-2-[4-hydroxy-3-(hydroxymethyl)phenyl]ethyl}-amino)hexyl]oxy}butyl)phenyl]imidazolidine-2,4-dione and salts, solvates, and physiologically functional derivatives thereof.

Salts and solvates of compounds of formulae (I), (Ia), (Ib) and (Ic) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formulae (I), (Ia), (Ib) and (Ic) and their pharmaceutically acceptable salts, solvates, and physiologically functional derivatives.

By the term "physiologically functional derivative" is meant a chemical derivative of a compound of formula (I), (Ia), (Ib) or (Ic) having the same physiological function as the free compound of formula (I), (Ia) (Ib) and (Ic), for example, by being convertible in the body thereto. According to the present invention, examples of physiologically functional derivatives include esters.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example, phenyl, methyl , methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Pharmaceutically acceptable esters of the compounds of formula (I), (Ia), (Ib) and (Ic) may have a hydroxyl group converted to a $C_{1-6}$alkyl, aryl, aryl $C_{1-6}$ alkyl, or amino acid ester.

As mentioned above, the compounds of formulae (I), (Ia), (Ib) and (Ic) are selective $\beta_2$-adrenoreceptor agonists as demonstrated using functional or reporter gene readout from cell lines transfected with human beta-adrenoreceptors as described below. Compounds according to the present invention also have the potential to combine long duration of effect with rapid onset of action. Furthermore, certain compounds have shown an improved therapeutic index in animal models relative to existing long-acting $\beta_2$-agonist bronchodilators. As such, compounds of the invention may be suitable for once-daily administration.

Therefore, compounds of formulae (I), (Ia), (Ib) and (Ic) and their pharmaceutically acceptable salts, solvates, and physiologically functional derivatives have use in the prophylaxis and treatment of clinical conditions for which a selective $\beta_2$-adrenoreceptor agonist is indicated. Such conditions include diseases associated with reversible airways obstruction such as asthma, chronic obstructive pulmonary diseases (COPD) (e.g. chronic and wheezy bronchitis, emphysema), respiratory tract infection and upper respiratory tract disease.

Other conditions which may be treated include premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

Accordingly, the present invention provides a method for the prophylaxis or treatment of a clinical condition in a mammal, such as a human, for which a selective $\beta_2$-adrenoreceptor agonist is indicated, which comprises administration of a therapeutically effective amount of a compound of formula (I), (Ia), (Ib) and (Ic), or a pharmaceutically acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a compound of formula (I), (Ia), (Ib) or (Ic) or a pharmaceutically acceptable salt, solvate, or physiologically functional derivative thereof for use in medical therapy, particularly, for use in the prophylaxis or treatment of a clinical condition in a mammal, such as a human, for which a selective $\beta_2$-adrenoreceptor agonist is indicated. In particular, there is provided a compound of formula (I), (Ia), (Ib) or (Ic) or a pharmaceutically acceptable salt, solvate, or physiologically functional derivative thereof for the prophylaxis or treatment of a disease associated with reversible airways obstruction such as asthma, chronic obstructive pulmonary disease (COPD), respiratory tract infection or upper respiratory tract disease. In a further aspect, there is provided a compound of formula (I), (Ia), (Ib) or (Ic) or a pharmaceutically acceptable salt, solvate, or physiologically functional derivative thereof for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a compound of formula (I), (Ia), (Ib) or (Ic) or a pharmaceutically acceptable salt, solvate, or physiologically functional derivative thereof in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease. In a further aspect, there is provided a compound of formula (I), (Ia), (Ib) or (Ic), or a pharmaceutically acceptable salt, solvate, or physiologically functional derivative thereof in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a compound of formula (I), (Ia), (Ib) or (Ic), or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered by inhalation at a dose of from 0.0005 mg to 10 mg, preferably 0.005 mg to 0.5 mg. The dose range for adult humans is generally from 0.0005 mg to 100mg per day and preferably 0.01 mg to 1 mg per day.

While it is possible for the compound of formula (I), (Ia), (Ib) or (Ic), or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I), (Ia), (Ib) or (Ic) or a pharmaceutically acceptable salt, solvate, or physiologically functional derivative thereof, and a pharmaceutically acceptable carrier or excipient, and optionally one or more other therapeutic ingredients.

Hereinafter, the term "active ingredient" means a compound of formula (I), (Ia), (Ib) or (Ic), or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Dry powder compositions for topical delivery to the lung by inhalation may, for example, be presented in capsules and cartridges of for example gelatine, or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 20 µg–10 mg of the compound of formula (I) optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetrafluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1–10 μm, preferably 2–5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60–90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), other $β_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, another $β_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9αa-difluoro-11β-hydroxy-16α-methyl-3-oxo-17α-propionyloxy-androsta-1,4-diene-17β-carbothioic acid S(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $β_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) in combination with a phosphodiesterase 4 (PDE4) inhibitor or a mixed PDE3/ PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

Initial experiments may be conducted to establish and validate a [$^3$H]-rolipram binding assay. Details of this work are given in the Binding Assays described in detail below.

Phosphodiesterase and Rolipram Binding Assays

Assay Method 1A

Isolated human monocyte PDE4 and hrPDE (human recombinant PDE4) was determined to exist primarily in the low affinity form. Hence, the activity of test compounds against the low affinity form of PDE4 can be assessed using standard assays for PDE4 catalytic activity employing 1 μM [$^3$H]cAMP as a substrate (Torphy et al., J. of Biol. Chem., Vol. 267, No. 3 pp1798–1804, 1992).

Rat brain high speed supernatants were used as a source of protein and both enantiomers of [$^3$H]-rolipram were prepared to a specific activity of 25.6 Ci/mmol. Standard assay conditions were modified from the published procedure to be identical to the PDE assay conditions, except for the last of the cAMP: 50 mM Tris HCl (pH 7.5), 5 mM $MgCl_2$, 50 μM 5'-AMP and 1 nM of [$^3$H]-rolipram (Torphy et al., J. of Biol. Chem., Vol. 267, No. 3 pp1798–1804, 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [$^3$H]-cAMP was not present.

Assay Method 1B

Measurement of Phosphodiesterase Activity

PDE activity was assayed using a [$^3$H]cAMP SPA or [$^3$H]cGMP SPA enzyme assay as described by the supplier (Amersham Life Sciences). The reactions were conducted in 96-well plates at room temperature, in 0.1 ml of reaction buffer containing (final concentrations): 50 mM Tris-HCl, pH 7.5, 8.3 mM $MgCl_2$, 1.7 mM EGTA, [$^3$H]cAMP or [$^3$H]cGMP (approximately 2000 dpm/pmol), enzyme and various concentrations of the inhibitors. The assay was allowed to proceed for 1 hr and was terminated by adding 50 μl of SPA yttrium silicate beads in the presence of zinc sulfate. The plates were shaken and allowed to stand at room temperature for 20 min. Radiolabeled product formation was assessed by scintillation spectrometry.

[$^3$H]R-Rolipram Binding Assay

The [$^3$H]R-rolipram binding assay was performed by modification of the method of Schneider and co-workers, see Nicholson, et al., Trends Pharmacol. Sci., Vol. 12, pp.19–27 (1991) and McHale et al., Mol. Pharmacol., Vol.39, 109–113 (1991). R-Rolipram binds to the catalytic site of PDE4 see Torphy et al., Mol. Pharmacol., Vol. 39, pp. 376–384 (1991). Consequently, competition for [$^3$H]R-rolipram binding provides an independent confirmation of the PDE4 inhibitor potencies of unlabeled competitors. The assay was performed at 30° C. for 1 hr in 0.5 μl buffer containing (final concentrations): 50 mM Tris-HCl, pH 7.5, 5 mM $MgCl_2$, 0.05% bovine serum albumin, 2 nM [$^3$H]R-rolipram (5.7×104 dpm/pmol) and various concentrations of non-radiolabeled inhibitors. The reaction was stopped by the addition of 2.5 ml of ice-cold reaction buffer (without [$^3$H]-R-rolipram) and rapid vacuum filtration (Brandel Cell Harvester) through Whatman GF/B filters that had been soaked in 0.3% polyethylenimine. The filters were washed with an additional 7.5 ml of cold buffer, dried, and counted via liquid scintillation spectrometry.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Examples of useful PDE4 inhibitors are:

(R)-(+)-1-(4-bromobenzyl)4-[(3-cyclopentyloxy)-4-methoxyphenyl]-2-pyrrolidone;

(R)-(+)-1-(4-bromobenzyl)-4-[(3-cyclopentyloxy)-4-methoxyphenyl]-2-pyrrolidone;

3-(cyclopentyloxy-4-methoxyphenyl)-1-(4-N'-[N2-cyano-S-methyl-isothioureido]benzyl)-2-pyrrolidone;

cis 4-cyano-4-(3-cyclopentyloxy-4methoxyphenyl)cyclohexan-1-carboxylic acid];

cis-[4-cyano-4-(3-cyclopropylmethoxy-4-difluoromethoxyphenyl)cyclohexan-1-ol];

(R)-(+)-ethyl [4-(3-cyclopentyloxy-4-methoxyphenyl)pyrrolidine-2-ylidene]acetate; and (S)-(–)-ethyl [4-(3-cyclopentyloxy-4-methoxyphenyl)pyrrolidine-2-ylidene]acetate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other compounds of interest include:

Compounds set out in U.S. Pat. No. 5,552,438 issued 3 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD-12–281 from Asta Medica (Hofgen, N. et al. 15th EFMC Int Symp Med Chem (September 6–10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19–23, Geneva) 1998] 1998, 12 (Suppl. 28): Abst P2393); roflumilast (CAS reference No 162401-32-3) and a pthalazinone (WO99/147505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/ PDE4 inhibitor which has been prepared and published on by Byk-Gulden, now Altana; arofylline under development by Almirall-Prodesfarma; VM554/ UM565 from Vernalis; or T-440 (Tanabe Seiyaku; Fuji, K. et al. J Pharmacol Exp Ther,1998, 284(1): 162), and T2585.

Other possible PDE-4 and mixed PDE3/ PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

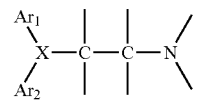

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Examples of preferred anti-histamines include methapyrilene and loratadine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a corticosteroid.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a corticosteroid.

The invention thus provides, in a further aspect, a combination comprising a compound of formula (I) a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may bib administered either sequentially or simultaneously in separate or combined pharmaceutical formulations. Appropriate doses of known therapeutic agents will be readily appreciated by those skilled in the art.

According to a further aspect of the invention, there is provided a process for preparing a compound of formula (I), (Ia), (Ib) or (Ic) or a salt, solvate, or physiologically functional derivative thereof which comprises a process (a),b), (c), (d) or (e) as defined below followed by the following steps in any order:
(i) optional removal of any protecting groups;
(ii) optional separation of an enantiomer from a mixture of enantiomers;
(iii) optional conversion of the product to a corresponding salt, solvate, or physiologically functional derivative thereof.

In one general process (a), a compound of formula (I), (Ia), (Ib) or (Ic) may be obtained by deprotection of a protected intermediate, for example of formula (II):

Examples of suitable amino protecting groups represented by $R^{14}$ include benzyl, α-methylbenzyl, diphenylmethyl, triphenylmethyl, benzyloxycarbonyl, tert-butoxycarbonyl, and acyl groups such as trichloroacetyl or trifluoroacetyl.

As will be appreciated by the person skilled in the art, use of such protecting groups may include orthogonal protection of groups in the compounds of formula (II) to facilitate the selective removal of one group in the presence of another, thus enabling selective functionalisation of a single amino or hydroxyl function. For example, the —CH(OH) group may be orthogonally protected as —CH(OR$^{18}$) using, for example, a trialkylsilyl group such as triethylsilyl. A person skilled in the art will also appreciate other orthogonal protection strategies, available by conventional means as described in Theodora W Greene and Peter G M Wuts (see above).

The deprotection to yield a compound of formula (I), (Ia), (Ib) or (Ic) may be effected using conventional techniques. Thus, for example, when $R^{12}$, $R^{13}$, and/or $R^{14}$ is an aralkyl group, this may be cleaved by hydrogenolysis in the presence of a metal catalyst (e.g. palladium on charcoal).

When $R^{12}$ and/or $R^{13}$ is tetrahydropyranyl this may be cleaved by hydrolysis under acidic conditions. Acyl groups represented by $R^{14}$ may be removed by hydrolysis, for example with a base such as sodium hydroxide, or a group

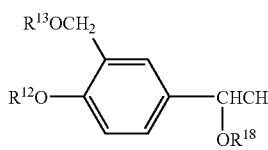

(II)

or a salt or solvate thereof, wherein $R^1$, $R^2$, $R^3$, $R^4$, $R^5$, m, and n are as defined for the compound of formula (I), (Ia), (Ib) or (Ic), and $R^{12}$, $R^{13}$, and $R^{14}$ are each independently either hydrogen or a protecting group provided that at least one of $R^{12}$, $R^{13}$, and $R^{14}$ is a protecting group, and $R^{18}$ is either hydrogen or a protecting group.

Suitable protecting groups may be any conventional protecting group such as those described in "Protective Groups in Organic Synthesis" by Theodora W Greene and Peter G M Wuts, 3rd edition (John Wiley & Sons, 1999). Examples of suitable hydroxyl protecting groups represented by $R^{12}$ and $R^{13}$ are esters such as acetate ester, aralkyl groups such as benzyl, diphenylmethyl, or triphenylmethyl, and tetrahydropyranyl.

such as trichloroethoxycarbonyl may be removed by reduction with, for example, zinc and acetic acid. Other deprotection methods may be found in Theodora W Greene and Peter G M Wuts (see above). In a particular embodiment of process (a), R$_{12}$ and $R^{13}$ may together represent a protecting group as in the compound of formula (III):

(III)

or a salt or solvate thereof, wherein $R^1$, $R^2$, $R^3$, $R^4$, $R^5$, $R^{14}$, $R^{18}$ m, and n are as defined for the compound of formula (I), (Ia), (Ib) or (Ic), $R^{15}$ and $R^{16}$ are independently selected from hydrogen, $C_{1-6}$alkyl, or aryl. In a preferred aspect, both $R^{15}$ and $R^{18}$ are methyl.

The compound of formula (III) may be converted to a compound of formula (I), (Ia), (Ib) or (Ic) by hydrolysis with dilute aqueous acid, for example acetic acid or hydrochloric acid in a suitable solvent or by transketalisation in an alcohol, for example ethanol, in the presence of a catalyst such as an acid (for example, toluenesulphonic acid) or a salt (such as pyridinium tosylate) at normal or elevated temperature.

It will be appreciated that the protecting groups $R^{12}$, $R^{13}$, $R^{14}$ and $R^{18}$ (including the cyclised protecting group formed by $R^{15}$ and $R^{16}$ as depicted in formula (III) may be removed in a single step or sequentially. The precise order in which protecting groups are removed will in part depend upon the nature of said groups and will be readily apparent to the skilled worker. Preferably, when $R^{15}$ and $R^{16}$ together form a protecting group as in formula (III) this protecting group is removed together with any protecting group on the CH(OH) moiety, followed by removal of $R^{14}$.

Depending on the nature of the group $R^6$, some compounds of formulae (II) and (III) wherein $R^{14}$ is hydrogen may be prepared from the corresponding compound of formula (IV):

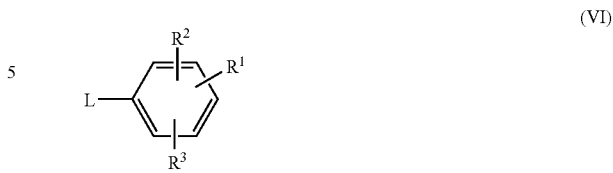

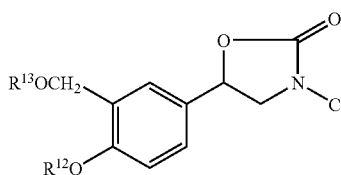

or a salt or solvate thereof, wherein $R^1$, $R^2$, $R^3$, $R^4$, $R^5$, $R^{12}$, $R^{13}$, m, and n are as defined for the compound of formula (II) or (III).

In this process, the group $R^6$ should be chosen such that it is sufficiently stable to resist hydrolysis under the conditions required to open the oxazolidine ring in the compound of formula (IV) to give a compound of formula (II) or (III).

The conversion of a compound of formula (IV) to a compound of formula (II) or (III) may be effected by treatment with a base, for example a non-aqueous base, such as potassium trimethylsilanolate, or an aqueous base such as aqueous sodium hydroxide, in a suitable solvent such as tetrahydrofuran.

Compounds of formula (IV) may be prepared from the corresponding compound of formula (V):

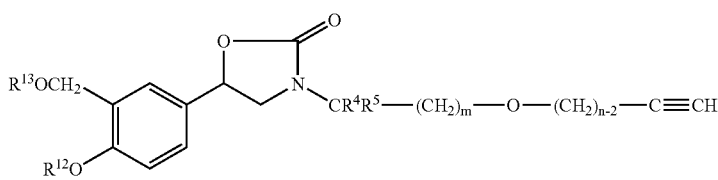

or a salt or solvate thereof, wherein $R^4$, $R^5$, $R^{12}$, $R^{13}$, m and n are as defined for the compound of formula (II);

by coupling with a compound of formula (VI) or a precursor thereof:

wherein $R^1$, $R^2$, and $R^3$ are as defined for the compound of formula (I) or each may independently represent a precursor for said groups, and L is a leaving group, such as a halo group (typically, bromo or iodo) or a haloalkyl sulphonate (typically, trifluoromethanesulphonate), followed by reduction.

The coupling of a compound of formula (V) with a compound of formula (VI) or a precursor thereof is conveniently effected in the presence of a catalyst system such as bis(triphenylphosphine) palladium dichloride with an organic base such as a trialkylamine, for example triethylamine, in a suitable solvent for example acetonitrile or dimethylformamide. The resulting alkyne may then be reduced, either with or without being isolated to form the compound of formula (IV). The reduction may be effected by any suitable method such as hydrogenation in the presence of a catalyst, for example palladium/charcoal or platinum oxide.

Compounds of formula (VI) are commercially available or may be prepared by methods well known to the person skilled in the art.

A suitable precursor of the compound of formula (VI) would be a compound of formula (VI) in which one or more of the substituents $R^1$, $R^2$, and $R^3$ is a group which is convertible to the desired group $R^1$, $R^2$, and/or $R^3$. For example, when $R^1$ is to be —$XR^6$ and $R^6$ is to be the group (a), a suitable precursor of the compound of formula (VI) may have the primary amine in place of the substituent $R^6$, such that the desired substituent $R^1$ may be formed by reaction with an appropriate isocyanate to give an urea group —XNHC(O)NHCH$_2$C(O)O(C$_{1-6}$alkyl). Conversion to the desired group R$^1$ may then be effected by standing the urea in an inert solvent, optionally in the presence of a base such as an inorganic base, for example potassium carbonate or sodium hydride, or an organic base, for example triethylamine or diisopropylethylamine, either before or after the coupling with the compound of formula (V). Alternatively the urea ester group depicted above may be hydrolysed to the corresponding urea carboxylic acid, followed by treatment with a mineral acid such as hydrochloric acid, or a strong organic acid such as as p-toluenesulphonic acid, to give the desired hydantoin group. The primary as amine may be formed by reduction of a corresponding nitro group.

As a further example, when the group R$^1$ is to be —XR$^6$ and R$^6$ is to be the group (b), a suitable precursor might have a primary urea in place of the group R$^6$, such that the desired substituent R$^1$ may be formed by reaction with an appropriate compound of formula (C$_{1-6}$alkyl)O$_2$CCR$^8$R$^9$L, wherein L is a leaving group as in the compound of formula (VI), typically chloro.

As a yet further example, when the group R$^1$ is to be —XR$^6$ and R$^6$ is to be the group (c), a suitable precursor might have a formyl group or a group —C(O)R$^8$ in place of the group R$^6$, such that the desired substituent R$^1$ may be formed by reaction with NaCN and (NH$_4$)$_2$CO$_3$ as in G. Wagner, B. Voigt and I. Lischke, Pharmazie, 1981, 36, 467.

As a still further example, when the group R$^1$ is to be —XR$^6$ and R$^6$ is to be the group (d), a suitable precursor might have a primary amine in place of the group R$^6$, such that the desired substituent R$^1$ may be formed by reaction with an appropriate isocyanate to give a urea group —NHC(O)NHCH$_2$CH$_2$L, wherein L is a leaving group as in the compound of formula (VI), typically chloro. Conversion to the desired group R$^1$ may then be effected by standing the urea in an inert solvent, for example N,N-dimethylformamide, in the presence of a base such as an inorganic base, for example potassium carbonate or sodium hydride, or an organic base, for example triethylamine or diisopropylethylamine, either before or after the coupling with the compound of formula (V).

As another example, if the group R$^1$ is to be —XR$^6$ and R$^6$ is to be the group (f), a suitable precursor might have an isocyanate in place of the group R$^6$. Conversion to the desired group R$^6$ could then be effected by reaction with a masked amino-aldehyde of formula H$_2$NCH$_2$CH(OC$_{1-6}$alkyl))$_2$ in an inert solvent such as dichloromethane. Cyclization to the desired R$^6$ group could then be effected by unmasking the aldehyde, for example by treatment with an acid such as aqueous trifluoroacetic acid, as in E. R. Parmee et al., Bioorg. Med. Chem. Lett. 1999, 9, 749–754.

As a further example, if the group R$^1$ is to be XR$^6$ and R$^6$ is to be the group (g) a suitable precursor might have a group —COCH$_2$NH$_2$ in place of R$^6$. Conversion to the desired group R$^6$ may be effected by treating with cyanic acid, according to the procedure described by Rupe, Chem. Ber 1894, 27, 582.

As another example, if the group R$^1$ is to be —CH$_2$R$^6$ and R$^6$ is to be the group (h), a suitable precursor might have a group Br in place of the group R$^6$, such that the desired substituent R$^1$ may be formed by coupling with the anion derived by deprotonation of parabanic acid or a suitable derivative thereof, for example by treatment with sodium hydride. Alternatively, if the group R$^1$ is to be —R$^6$ and R$^6$ is to be the group (h), a suitable precursor might have an iodo group in place of the group R$^6$, such that the desired substituent R$^1$ may be formed by a palladium catalysed condensation with parabanic acid or a suitable derivative thereof.

An alternative precursor when R$^1$ is to be —XR$^6$ and R$^6$ is to be the group (h) would have a primary urea in place of the group R$^6$. Conversion to the desired group R$^6$ could then be effected by reaction with (C$_{1-6}$alkyl)O$_2$CCOCl.

As another example, if the group R$^1$ is to be XR$^6$ and R$^6$ is to be the group (i), a suitable precursor might have a group —NHOH in place of the group R$^6$. Conversion to the desired group R$^6$ could then be effected by reaction with chlorocarbonylisocyanate as in M. S. Malamas et el, Eur. J. Med. Chem. 2001, 36, 31–42.

As another example, if the group R$^1$ is to be XR$^6$ and R$^6$ is to be the group (j), a suitable precursor might have a group —NHNH$_2$ in place of the group R$^6$. Conversion to the desired group R$^6$ could then be effected by reaction with urea in a solvent such as N,N-dimethylformamide, as in J. A. Lenoir and B. L. Johnson, Tetrahedron Letters, 1973, 5123–5126.

As a still further example, when R$^1$ is to be the group XR$^6$ and Re is to be the group (k) a suitable precursor might have an isocyanate in place or the group R$^6$ such that the desired substituent R$^1$ may be formed by treating the isocyanate with hydroxylamine and a chloroformate, eg. an alkyl chloroformate such as ethyl chloroformate, and treating the resulting compound with base, eg. NaOH, to form the desired heterocyclic ring. (G. Zinner and R. Weber, Arch. Pharm. Ber. 1965, 298, 580–587).

As another example, when the group R$^1$ is to be XR$^6$ and R$^6$ is to be the group (I) a suitable presursor might be an isocyanate in place of the group R$^6$. This may be treated with an alkyl carbazate eg. ethyl carbazate and the resulting product treated with a base eg. potassium hydroxide to form the desired heterocycle (W Adam and N Carballeira J. Am. Chem. Soc., 1984, 106, 2874).

Compounds of formula (V) may be prepared by coupling a compound of formula (VII):

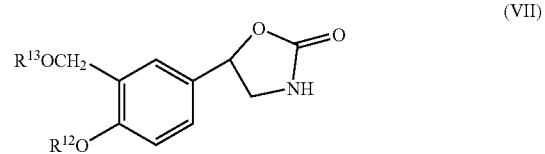

(VII)

or a salt or solvate thereof, wherein R$^{12}$ and R$^{13}$ are as defined for the compound of formula (V) with a compound of formula (VIII):

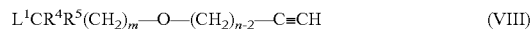

L$^1$CR$^4$R$^5$(CH$_2$)$_m$—O—(CH$_2$)$_{n-2}$—C≡CH (VIII)

Wherein R$^4$, R$^5$, m and n are as defined for the compound of formula (V) and L$^1$ is a leaving group, for example a halo group, (typically bromo or iodo) or a sulphonate such as an alkyl sulphonate (typically methane sulphonate) an aryl sulphonate (typically toluenesulphonate) or a haloalyalkylksulphonate (typically trifluoromethane sulphonate).

The coupling of a compound of formula (VII) with a compound of formula (VIII) may be effected in the presence of a base, such as a metal hydride, for example sodium hydride, or an inorganic base such as cesium carbonate, in an aprotic solvent, for example N,N-dimethylformamide.

Compounds of formula (VIII) may be prepared from the corresponding dihaloalkane and hydroxyalkyne by conventional chemistry, typically in the presence of an inorganic base, such as aqueous sodium hydroxide, under phase transfer conditions in the presence of a salt such as tetraalkylammonium bromide.

Compounds of formula (VII) may be prepared by ring closure of a compound of formula (IX):

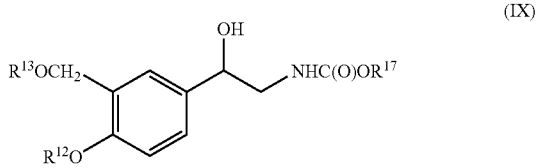

wherein $R^{12}$ and $R^{13}$ are as defined for the compound of formula (VII) and $R^{17}$ is $C_{1-6}$alkyl, for example tert-butyl, or aryl, for example phenyl. The ring closure may be effected by treatment with a base, such as a metal hydride, for example sodium hydride, in the presence of an aprotic solvent, for example, N,N-dimethylformamide.

Compounds of formula (IX) may be prepared from the corresponding ketone of formula (X):

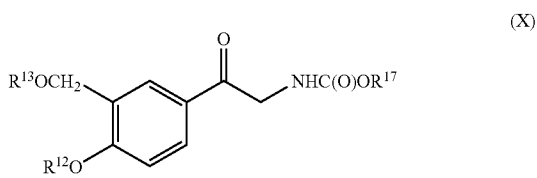

wherein $R^{12}$ and $R^{13}$ and $R^{17}$ are as defined for the compound of formula (IX), by reduction by any suitable method, for example by treatment with borane, in the presence of a chiral catalyst, such as CBS-oxazaborolidine, in a suitable solvent such as tetrahydrofuran.

The compound of formula (X) may be prepared from the corresponding halide of formula (XI):

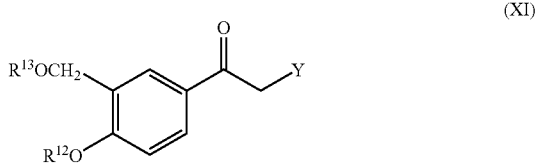

wherein $R^{12}$ and $R^{13}$ are as defined for the compound of formula (IV) and Y is a halo, suitably bromo.

The conversion of a compound of formula (XI) to a compound of formula (X) may be effected by reaction with the protected amine $HN(COOR^{17})_2$ wherein $R^{17}$ is as defined for the compound of formula (X) in the presence of an inorganic base such as cesium carbonate, followed by selective removal of one of the $COOR^{17}$ groups, for example by treatment with an acid such as trifluoroacetic acid.

Compounds of formula (XI) may be prepared from the corresponding compound having free hydroxymethyl and hydroxy substituents (which itself may be prepared from 2-bromo-1-(4-hydroxy)-3-hydroxymethyl-phenethyl)ethanone, the preparation of which is described in GB2140800, by treatment with 2-methoxypropane in acetone in the presence of an acid e.g. p-toluenesulphonic acid in a nitrogen atmosphere or by other standard methods) by forming the protected groups $R^{13}OCH_2—$ and $R^{12}O—$ wherein $R^{13}$ and $R^{12}$ are as defined for the compound of formula (XI). Such methods are described in DE 3513885 (Glaxo).

Compounds of formulae (II) or (III) where $R^{14}$ is hydrogen or a protecting group may be prepared according to the general methods described below.

In a further process (b) a compound of formula (I), (Ia), (Ib) or (Ic) may be obtained by alkylation of an amine of formula (XII):

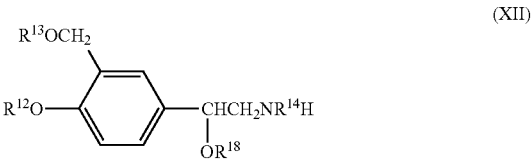

wherein $R^{12}$, $R^{13}$, $R^{14}$ and $R^{18}$ are each independently either hydrogen or a protecting group. Suitable protecting groups are discussed in the definition of compounds of formula (II) and (III); with a compound of formula (XIII):

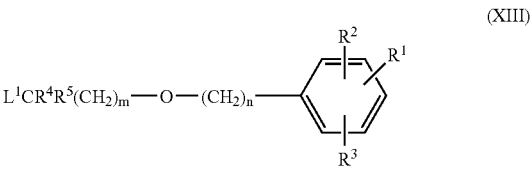

wherein $R^1$, $R^2$, $R^3$, $R^4$, $R^5$, m, and n are as defined for the compound of formula (I), (Ia) or (Ib) and $L^1$ is a leaving group as herein before defined for the compound of formula (VIII); followed by removal of any protecting groups present by conventional methods as described above for the deprotection of compounds of formula (II) and (III). For speed of reaction, $L^1$ is preferably bromo or is converted to bromo in situ, from the corresponding compound wherein $L^1$ is methanesulphonate, for example by addition of tetrabutylammonium bromide to the reaction mixture.

The compound of formula (I), (Ia) or (Ib) may be formed directly (when in the compound of formula (XII) $R^{12}$, $R^{13}$, $R^{14}$ and $R^{18}$ are each hydrogen) or via a compound of formula (II) or (III) which may or may not be isolated (when in the compound of formula (XII) at least one of $R^{12}$, $R^{13}$ $R^{14}$ and $R^{18}$ is a protecting group).

The reaction of compounds of formulae (XII) and (XIII) is optionally effected in the presence of an organic base such as a trialkylamine, for example, diisopropylethylamine, and in a suitable solvent for example N,N-dimethylformamide, or acetonitrile.

Compounds of formula (XII) are known in the art (for example EP-A 0947498) or may be readily prepared by a person skilled in the art, for example from the corresponding halide of formula (XI) as defined above. The conversion of a compound of formula (XI) to a compound of formula (XII) may be effected by reaction with sodium azide in a suitable solvent, for example N,N-dimethylformamide, to give the corresponding compound wherein Y denotes $N_3$. The carbonyl group may then be reduced to the corresponding alcohol by any suitable method, for example by treatment with borane, in the presence of a chiral catalyst, such as (R)-tetrahydro-1-methyl-3,3-diphenyl-1H,3H-pyrrolo[1,2-c][1,3,2]oxazaborole, in a suitable solvent such as tetrahydrofuran. The azide group may be reduced to the corresponding amine group by any suitable method, for example by catalytic hydrogenation in the presence of a catalyst such as palladium/charcoal or platinum oxide.

Compounds of formula (XIII) may be prepared by coupling a compound of formula (VI) or a precursor thereof (wherein one or more of the substituents $R^1$, $R^2$, or $R^3$ is a group which is convertible to $R^1$, $R^2$, or $R^3$) with a compound of formula (VII) as shown above, followed by reduction.

The coupling of a compound of formula (VIII) with a compound (VI) may be effected by in the presence of a catalyst system such as bis (triphenylphosphine) palladium dichloride with an organic base such as a trialkylamine, for example, triethylamine, in a suitable solvent, for example acetonitrile or N,N-dimethylformamide. The resulting alkyne may then be reduced, either with or without being isolated, to form the compound of formula (XIII). The reduction may be effected by any suitable method such as hydrogenation in the presence of a catalyst, for example, palladium/charcoal or platinum oxide. If necessary, the substituents $R^1$, $R^2$, and/or $R^3$ may be formed by conventional conversions where a precursor is present.

In a yet further process (c) a compound of formula (I), (Ia), (Ib) or (Ic) may be obtained by reduction of a compound of formula (XIV):

wherein $R^1$, $R^2$, $R^3$, $R^4$, $R^5$, m and n are as defined for formula (I) and $R^{12}$, $R^{13}$, $R^{14}$ and $R^{18}$ each independently represent a hydrogen atom or a protecting group as defined above.

The reduction may be effected by any suitable method such as hydrogenation in the presence of a catalyst, for example, palladium/charcoal or platinum oxide.

It will be appreciated that where $R^{12}$, $R^{13}$, $R^{14}$ and $R^{18}$ each represent hydrogen, the reduction will yield a compound of formula (I), but where one or more or $R^{12}$, $R^{13}$, $R^{14}$ and $R^{18}$ represent a protecting group then reduction will yield a compound of formula (II) or (III), which may then be deprotected to give a compound of formula (I).

A compound of formula (XIV) may be prepared by reacting a compound of formula (XII) as herein before defined with a compound of formula (XV):

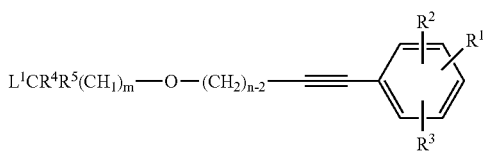

(XV)

wherein $R^1$, $R^2$, $R^3$, $R^4$, $R^5$, m, and n are as defined for the compound of formula (I), (Ia) or (Ib) and $L^1$ is as defined for the compound of formula (XIII).

The reaction of compounds of formulae (XIV) and (XV) is optionally effected in the presence of an organic base such as a trialkylamine, for example, diisopropylethylamine, and in a suitable solvent for example N,N-dimethylformamide.

The compound of formula (XV) may be prepared by coupling a compound of formula (VI) as defined above with a compound of formula (VIII) as defined above, as described for the first stage of the preparation of compounds (XIII), without the reduction step.

An alkyne of formula (XV) may also be prepared by reacting a compound of formula (XVI):

$$L^2CR^4R^5(CH_2)mL^3 \qquad (XVI)$$

Wherein $R^4$, $R^5$ and n are as defined hereinabove and $L^2$ and $L^3$ each represent a leaving group, which groups may independently be selected for example from those defined above for L and $L^1$, with a compound of formula (XVII):

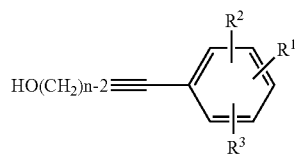

using conventional methods, for example as described for the preparation of compounds (VIII).

Compounds of formula (XVII) may be prepared by reacting a hydroxyalkyne

with a compound of formula (VI) using methods analogous to those described above for coupling a compound (V) with a compound (VI).

In a further process (d) a compound of formula (I), (Ia), (Ib) or (Ic) may be prepared by reacting a compound of formula (XVIII):

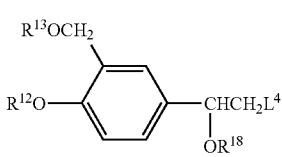 (XVIII)

wherein $R^{12}$, $R^{13}$ and $R^{18}$ are as hereinbefore defined and $L^4$ is a leaving group, is reacted with an amine of formula (XIX):

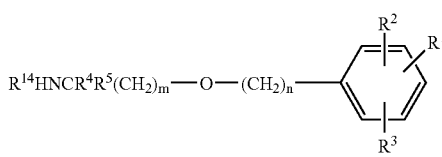 (XIX)

followed by removal of any protecting groups present by conventional methods as described above for the deprotection of compounds of formula (II).

The reaction may be effected using conventional conditions for such displacement reactions.

Compounds of formula (XVIII) may be prepared by methods known in the art.

Compounds of formula (XIX) may be prepared by reacting a compound of formula (XIII) with an amine $R^{14}NH_2$.

In a further process (e) a compound of formula (I), (Ia) or (Ib) may be prepared by removal of a chiral auxiliary from a compound of formula (IIa):

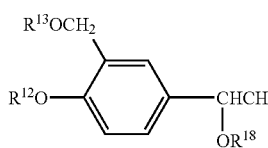 (IIa)

wherein $R^1$, $R^2$, $R^3$, $R^4$, $R^5$, m and n are as defined for formula (I), $R^{12}$, $R^{13}$, $R^{14}$ and $R^{18}$ each independently represent a hydrogen atom or a protecting group as defined above and $R^{19}$ represents a chiral auxiliary.

A "chiral auxiliary" is a moiety that is introduced into a molecule to influence the stereochemistry of the product formed, and is removed in whole or part at a later time. A chiral auxiliary may simultaneously function as a protecting group.

Many chiral auxiliaries are commercially available, and persons skilled in the art would choose one based on the properties desired i.e. the absolute stereochemistry desired and compatibility with the processes being used. Chiral auxiliaries suitable for use in this process include but are not limited to the S-isomer and/or the R-isomer of phenyl glycinol and substituted derivatives thereof.

The chiral auxiliary is preferably a moiety of the formula:

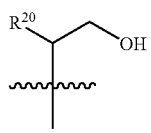

or a single enantiomer thereof, wherein $R^{20}$ represents $C_{1-6}$alkyl or optionally substituted phenyl or benzyl wherein the optional substitution is one or more independently selected from $C_{1-6}$alkyl, halogen, hydroxy, $C_{1-6}$alkoxy or nitro e.g. para-hydroxyphenyl.

More preferably the chiral auxiliary is a moiety:

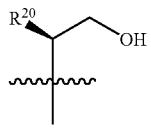

wherein $R^{20}$ is as defined above. Alternatively it may be a moiety of formula:

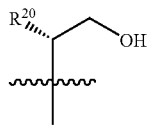

wherein $R^{20}$ is as defined above.

Preferably $R^{20}$ represents phenyl optionally substituted as described above. Most preferably $R^{20}$ represents unsubstituted phenyl.

The chiral auxiliary in this process may typically be removed by hydrogenolysis using for example a palladium on carbon catalyst or preferably using palladium hydroxide (Pearlman's catalyst). Advantageously when Pearlman's catalyst is used the removal of the chiral auxiliary is most efficient. This method of removal is especially suitable where $R^{20}$ is phenyl or a substituted phenyl. Alternatively the nitrogen, to which the auxiliary is attached, may be derivatised under oxidising conditions to form the N-oxide before elimination by heating to give a secondary amine.

A compound of formula (IIa) may be prepared by reduction of the corresponding alkyne of formula (XIVa):

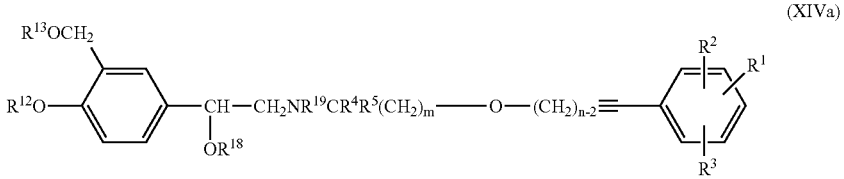

wherein $R^1$, $R^2$, $R^3$, $R^4$, $R^5$, m and n are as defined for formula (I) and $R^{12}$, $R^{13}$, $R^{14}$ and $R^{18}$ each independently represent a hydrogen atom or a protecting group as defined above. Preferably in the compounds of formulae (IIa) and (XIVa) the protecting groups $R^{12}$ and $R^{13}$ together form a group —$CR^{15}R^{16}$— as in the compounds of formula (III).

Reduction of an alkyne of formula (XIVa) may be effected by methods well known in the art, for example by catalytic hydrogenation, using palladium on charcoal or more preferably palladium hydroxide (Pearlman's catalyst). The chiral auxiliary may also be removed under reductive conditions. Advantageously, therefore the reduction of the alkyne and removal of the chiral auxiliary may be effected concomitantly in a 'one-pot' reaction.

An alkyne of formula (XIVa) may be prepared by reaction of a compound of formula (XX)

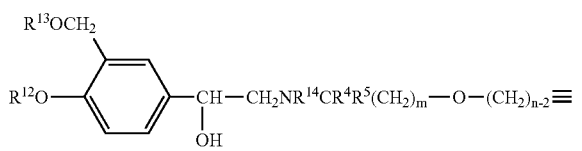

with a compound of formula (VI) under conditions described above for coupling of compounds (V) and (VI).

A compound of formula (XX) may be prepared by reacting a compound of formula (XIIa):

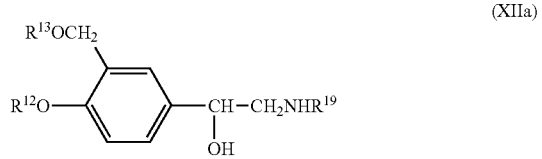

with an aldehyde of formula (XXI):

using known methods for effecting reductive amination, e.g. sodium triacetoxyborohydride in a solvent such as chloroform An aldehyde of formula (XXI) may be prepared from a corresponding halide of formula (VIII) using standard techniques such as treatment with sodium bicarbonate in a solvent such as DMSO at elevated temperature, preferably in the range 130–160° C.

A compound of formula (XIIa) may be prepared from a compound of formula (Xa):

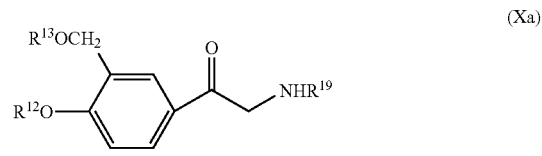

Wherein $R^{12}$, $R^{13}$ and $R^{19}$ are as hereinbefore defined by treatment with a reducing agent such as a hydride source e.g. sodium borohydride. Preferably this process takes place in the presence of an inert metal salt such as calcium chloride suitably at non-extreme temperatures e.g. below ambient, such as 0° C. This allows the desired stereochemistry to be introduced efficiently with good enantiomeric excess at an early stage in the synthesis, using inexpensive and relatively harmless reagents. Furthermore, the enantiomeric excess may be increased by recrystallisation of the product of this process.

A compound of formula (Xa) may be prepared from a compound of formula (XI) as hereinbefore defined by reaction with an appropriate chiral amine, e.g. (S)-phenylglycinol, in the presence of a non-nucleophilic base in an inert solvent at non-extreme temperatures.

A detailed description of a process analogous to Route (e) may be found in published International Application Number WO/0196278.

In the above process (e) it is preferred that the protecting groups $R^{12}$ and $R^{13}$ together form a protecting group as depicted in formula (III).

It will be appreciated that in any of the routes (a) to (e) described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

The enantiomeric compounds of the invention may be obtained (i) by separation of the components of the corresponding racemic mixture, for example, by means of a chiral chromatography column, enzymic resolution methods, or preparing and separating suitable diastereoisomers, or (ii) by direct synthesis from the appropriate chiral intermediates by the methods described above.

Optional conversions of a compound of formula (I), (Ia) or (Ib) to a corresponding salt may conveniently be effected by reaction with the appropriate acid or base. Optional conversion of a compound of formula (I), (Ia) or (Ib) to a corresponding solvate or physiologically functional derivative may be effected by methods known to those skilled in the art.

According to a further aspect, the present invention provides novel intermediates for the preparation of compounds of formula (I), (Ia) or (Ib), for example:

compounds of formula (II), (III) and XIV as defined above, or an optical isomer, a salt, or a protected derivative thereof; particularly, a compound selected from:

3-(3-{4-[(6-{[(2R)-2-(2,2-dimethyl-4H-1,3-benzodioxin-6-yl)-2-hydroxyethyl]amino}hexyl)oxy]butyl}phenyl)imidazolidine-2,4-dione;

3-(3-{3-[(7-{[(2R)-2-(2,2-dimethyl-4H-1,3-benzodioxin-6-yl)-2-hydroxyethyl]amino}heptyl)oxy]propyl}phenyl)imidazolidine-2,4-dione;

1-(3-{4-[(6-{[(2R)-2-(2,2-dimethyl-4H-1,3-benzodioxin-6-yl)-2-hydroxyethyl]amino}hexyl)oxy]butyl{phenyl)imidazolidine-2-one; and 1-(3-{4-[(6-{[(2R)-2-(2,2-dimethyl-4H-1,3-benzodioxin-6-yl)-2-hydroxyethyl]amino}hexyl)oxy]butyl}phenyl)imidazolidine-2,4-dione;

3-(3-{4-[(6-{[(2S)-2-(2,2-dimethyl-4H-1,3-benzodioxin-6-yl)-2-hydroxyethyl]amino}hexyl)oxy]butyl}phenyl)imidazolidine-2,4-dione;

3-(4-{4-[(6-{[(2R)-2-(2,2-dimethyl-4H-1,3-benzodioxin-6-yl)-2-hydroxyethyl]amino}hexyl)oxy]butyl}phenyl)imidazolidine-2,4-dione;

3-(2-{4-[(6-{[(2R)-2-(2,2-dimethyl-4H-1,3-benzodioxin-6-yl)-2-hydroxyethyl]amino}hexyl)oxy]butyl}phenyl)imidazolidine-2,4-dione;

3-(3-{4-[(6-{[(2R)-2-(2,2-dimethyl-4H-1,3-benzodioxin-6-yl)-2-hydroxyethyl]amino}hexyl)oxy]butyl}benzyl)imidazolidine-2,4-dione;

3-(3-{5-[(5-{[(2R)-2-(2,2-dimethyl-4H-1,3-benzodioxin-6-yl)-2-hydroxyethyl]amino}pentyl)oxy]pentyl}phenyl)imidazolidine-2,4-dione;

3-(3-{5-[(6-{[(2R)-2-(2,2-dimethyl-4H-1,3-benzodioxin-6-yl)-2-hydroxyethyl]amino}hexyl)oxy]pentyl}phenyl)imidazolidine-2,4-dione;

3-(3-{6-[(6-{[(2R)-2-(2,2-dimethyl-4H-1,3-benzodioxin-6-yl)-2-hydroxyethyl]amino}hexyl)oxy]hexyl}phenyl)imidazolidine-2,4-dione;

3-(3-{6-[(6-{[(2R)-2-(2,2-dimethyl-4H-1,3-benzodioxin-6-yl)-2-hydroxyethyl]amino}hexyl)oxy]hexyl}phenyl)imidazolidine-2,4-dione;

(5S)-5-(3-{4-[(6-{[(2R)-2-(2,2-dimethyl-4H-1,3-benzodioxin-6-yl)-2-hydroxyethyl]amino}hexyl)oxy]butyl}benzyl)-5-methylimidazolidine2,4-dione;

2-[3-(3-{4-[(6-{[(2R)-2-(2,2-dimethyl-4H-1,3-benzodioxin-6-yl)-2-hydroxyethyl]amino}hexyl)oxy]butyl}phenyl)-2,4-dioxoimidazolidin-1-yl]acetamide;

5-{4-[4-({6-[(5R)-5-(2,2-dimethyl-4H-1,3-benzodioxin-6-yl)-2-oxo-1,3-oxazolidin-3-yl]hexyl}oxy)butyl]benzyl}imidazolidine-2,4-dione;

3-(3-{4-[(6-{[(2R)-2-(2,2-dimethyl-4H-1,3-benzodioxin-6-yl)-2-hydroxyethyl]amino}hexyl)oxy]butyl}phenyl)-5,5-dimethylimidazolidine-2,4-dione;

3-(3-{3-[(7-{[(2R)-2-(2,2-dimethyl-4H-1,3-benzodioxin-6-yl)-2-hydroxyethyl]amino}heptyl)oxy]propyl}phenyl)-1-(methylsulfonyl)imidazolidine-2,4-dione;

1-(3-{3-[(6-{[(2R)-2-(2,2-dimethyl-4H-1,3-benzodioxin-6-yl)-2-hydroxyethyl]amino}hexyl)oxy]propyl}phenyl)imidazolidine-2,4-dione;

N-[1-(3-{4-[(6-{[(2R)-2-(2,2-dimethyl-4H-1,3-benzodioxin-6-yl)-2-hydroxyethyl]amino}hexyl)oxy]butyl}benzyl)-2,5-dioxoimidazolidin-4-yl]urea;

3-Benzyl-1-(3-{4-[(6-{[(2R)-2-(2,2-dimethyl-4H-1,3-benzodioxin-6-yl)-2-hydroxyethyl]amino}hexyl)oxy]butyl}phenyl]imidazolidine-2,4-dione;

1-(3-{4-[(6-{[(2R)-2-(2,2-dimethyl-4H-1,3-benzodioxin-6-yl)-2-hydroxyethyl]amino}hexyl)oxy]butyl{phenyl)-3-methylimidazolidine-2,4-dione;

Ethyl [3-(3-{4-[(6-{[(2-2-(2,2-dimethyl-4H-1,3-benzodioxin-6-yl)-2-hydroxyethyl]amino}hexyl)oxy]butyl}phenyl)-2,5-dioxoimidazolidin-1-yl]acetate;

2-[3-(3-{4-[(6-{[(2R)-2-(2,2-dimethyl-4H-1,3-benzodioxin-6-yl)-hydroxyethyl]amino}hexyl)oxy]butyl}phenyl)-2,5-dioxoimidazolidin-1-yl]acetamide;

1-(3-{4-[(6-{[(2R)-2-(2,2-dimethyl-4H-1,3-benzodioxin-6-yl)-2-hydroxyethyl]amino}hexyl)oxy]butyl}benzyl)imidazolidine-2,4-dione;

3-Benzyl-1-(3-{4-[(6-{[(2R)-2-(2,2-dimethyl-4H-1,3-benzodioxin-6-yl)-2-hydroxyethyl]amino}hexyl)oxy]butyl}phenyl)imidazolidine-2,4-dione;

3-(3-{4-[(6-{[(2R)-2-(2,2-imethyl-4H-1,3-benzodioxin-6-yl)-2-hydroxyethyl]amino{hexyl)oxy]butyl}phenyl)-1-(methylsulfonyl)imidazolidine-2,4-dione; and 4(3-{4-[(6-{[(2R)-2-(2,2-dimethyl-4H-1,3-benzodioxin-6-yl)-2-hydroxyethyl]amino}hexyl)oxy]butyl}phenyl)-1,2,4-triazolidine-3,5-dione.

For a better understanding of the invention, the following Examples are given by way of illustration.

SYNTHETIC EXAMPLES

Throughout the examples, the following abbreviations are used:
LCMS: Liquid Chromatography Mass Spectrometry
MS: mass spectrum
TSP+ve: thermospray mass spectrum positive mode
HPLC: high pressure liquid chromatography
RT: retention time
THF: tetrahydofuran
DMF: N,N-dimethylformamide
EtOAc: ethyl acetate
Et$_2$O: diethyl ether
EtOH: ethanol
MeOH: methanol
bp: boiling point
ca: circa
h: hour(s)
min: minute(s)

All temperatures are given in degrees centigrade.

Silica gel refers to Merck silica gel 60 Art number 7734.

Flash silica gel refers to Merck silica gel 60 Art number 9385.

Biotage refers to prepacked silica gel cartridges containing KP-Sil run on flash 12i chromatography module.

Bond Elut are prepacked cartridges used in parallel purifications, normally under vacuum. These are commercially available from Varian.

LCMS was conducted on a Supelcosil LCABZ+PLUS column (3.3 cm×4.6 mm ID) eluting with 0.1% HCO$_2$H and 0.01M ammonium acetate in water (solvent A), and 0.05% HCO$_2$H 5% water in acetonitrile (solvent B), using the following elution gradient 0–0.7 min 0% B, 0.7–4.2 min 100% B, 4.2–5.3 min 0% B, 5.3–5.5 min 0% B at 3 ml/min. The mass spectra were recorded on a Fisons VG Platform spectrometer using electrospray positive and negative mode (ES+ve and ES−ve).

HPLC was conducted on a LCABZ+PLUS column (3.3 cm×4.6 mm ID) elufing with 0.1% formic acid and 0.01M ammonium acetate in water (solvent A), and 0.05% formic

EXAMPLE 1

3-[3-(4-{[6-([(2R)-2-Hydroxy-2-[4-hydroxy-3-(hydroxymethyl)phenyl]ethyl}amino)hexyl]oxy}butyl)phenyl]imidazolidine-2,4-dione acetate i) 6-Bromohexyl but-3-ynyl ether 3-Butyn-1-ol (42.4 ml) was stirred vigorously with 1,6-dibromohexane (260 ml) and tetrabutylammonium bisulphate (2.4 g) in 50% aqueous sodium hydroxide solution (200 ml) under nitrogen for 3 days. Water (ca 700 ml) was added and the organic layer was separated. The aqueous layer was extracted twice with dichloromethane (2×100 ml) and the combined organic layers were washed with water, dried (MgSO$_4$) and concentrated. The residue in petroleum ether (bp 40–60°) was loaded onto a column of silica gel (1.5 kg) and the column was eluted with petroleum ether (bp 40–60°), then 10% diethyl ether in petroleum ether (bp 40–60°) to give the title compound (103.3 g).

ii) 1-{4-[(6-Bromohexyl)oxy]but-1-ynyl}-3-nitrobenzene

A mixture of 1-iodo-3-nitrobenzene (3 g), 6-bromohexyl but-3-ynyl ether (3 g), bis(triphenylphosphine)palladium (II) chloride (0.421 g), copper (I) iodide (0.114 g) in DMF (10 ml) and diisopropylethylamine (4 ml) was stirred under nitrogen at 20° C. for 5 h. The mixture was concentrated under reduced pressure and the residue was diluted in EtOAc and washed with 2M HCl, NaHCO$_3$, brine and dried (MgSO$_4$). The solvent was removed by evaporation and the residue was chromatographed on a Biotage column eluting with ether:petroleum ether(40–60° C.) (1:9) to give the title compound (4.12 g). LCMS RT=4.14 min iii) 6-{[4-(3-Nitrophenyl)but-3-ynyl]oxy}hexyl acetate A mixture of 1-{4-[(6-bromohexyl)oxy]but-1-ynyl}-3-nitrobenzene (4.18 g), sodium acetate (9.68 g), tetrabutylammonium bromide (384 mg) in DMF (15 ml) and water (10 ml) was heated to 75° C. for 6 h. The mixture was then allowed to cool to 20° C. and then extracted with Et$_2$O. The organic solution was concentrated and purified by chromatography on a Biotage (40 g) eluting with Et$_2$O-petroleum ether(1:19 increasing to 1:1) to give the title compound (2.973 g). LCMS RT=3.84 min.

iv) 6-[4-(3-Aminophenyl)butoxy]hexyl acetate

6-{[4-(3-Nitrophenyl)but-3-ynyl]oxy}hexyl acetate (2.973 g) was hydrogenated over PtO$_2$ (300 mg) in EtOH over 1 h. The catalyst was removed by filtration and washed with EtOH. The combined filtrate and washings were concentrated under reduced pressure to give the title compound (2.844 g) LCMS RT=3.30 min.

v) Ethyl N-({[3-(4-{[6-(acetyloxy)hexyl]oxy}butyl)phenyl]amino}carbonyl)glycinate 6-[4-(3-Aminophenyl)butoxy]hexyl acetate (2.84 g) in CH$_2$Cl$_2$ (30 ml) was treated with ethyl isocyanatoacetate (1.2 ml). After 0.75 h the mixture was treated with MeOH (2 ml) and stirred for 0.5 h. The mixture was concentrated, purified on a 10 g silica Bond Elut cartridge eluting with Et$_2$O-petroleum ether(1:1) and then with Et$_2$O to give the title compound (3.33 g) ES+ve 437 (MH)$^+$.

vi) 3-(3-{4-[(6-Hydroxyhexyl)oxy]butyl}phenyl)imidazolidine-2,4-dione

A solution of ethyl N-({[3-(4-{[6-(acetyloxy)hexyl]oxy}butyl)phenyl]amino}-carbonyl)glycinate (2.967 g) in ethanol (30 ml) was treated under nitrogen with sodium hydride (60% oil dispersion; 280 mg) and the mixture was stirred for 18 h. The solvent was removed under reduced pressure, the residue was dissolved in acetic acid (10 ml) and conc. HBr (1 ml) and the mixture was heated to 75° C. for 1 h. The solvent was removed under reduced pressure, the residue was partitioned between EtOAc and brine. The organic solution was washed with brine, dried and evaporated to dryness. The residue was dissolved in MeOH (30 ml), SOCl$_2$ (0.5 ml) was added, and the solution was stirred for 2 h. The solvent was removed under reduced pressure to give the title compound (2.67 g) ES+ve 349 (MH)$^+$.

vii) 6-{4-[3-(2,5-Dioxoimidazolidin-1-yl)phenyl]butoxy}hexyl methanesulfonate 3-(3-{4-[(6-Hydroxyhexyl)oxy]butyl}phenyl)imidazolidine-2,4-dione (2.67 g) in CH$_2$Cl$_2$ (50 ml) and triethylamine (1.2 ml) was treated with methanesulfonyl chloride (1.22 ml) and the mixture was stirred at 20° C. for 1.5 h. The mixture was diluted with CH$_2$Cl$_2$ and washed with 2M HCl, NaHCO$_3$, dried and purified by chromatography on Biotage (40 g) eluting with EtOAc-petroleum ether(1:1) and then with 2% MeOH—CH$_2$Cl$_2$ to give the title compound (1.186 g) ES+ve 427 (MH)$^+$.

viii) 2-Azido-1-(2,2-dimethyl-4H-1,3-benzodioxin-6-yl)ethanone

2-Bromo-1-(2,2-dimethyl-4H-1,3-benzodioxin-6-yl)ethanone (Glaxo DE 3513885, 1985) (52 g) in DMF (300 ml) was treated with sodium azide (12.24 g) and the mixture was stirred for 2 h at 20° C. The reaction mixture was diluted with EtOAc and washed with water and dried (MgSO$_4$). The solvent was removed under reduced pressure to give the title compound (39.11 g). TSP+ve 248(MH)$^+$.

ix) (1R)-2-Azido-1-(2,2-dimethyl-4H-1,3-benzodioxin-6-yl)ethanol (R)-Tetrahydro-1-methyl-3,3-diphenyl-1H,3H-pyrrolo[1,2-c][1,3,2]oxazaborole solution in toluene (1M, 7.5 ml) was added to THF (75 ml) and the solution was diluted to 0° C. Borane-THF complex (1M solution in THF, 125 ml) was added and the mixture was stirred under nitrogen for 15 min. A solution of 2-azido-1-(2,2-dimethyl-4H-1,3-benzodioxin-6-yl)ethanone (24.7 g) in THF (250 ml) was added dropwise over 1.5 h at 5° C. The mixture was stirred for a further 1 h and then cautiously treated with 2M HCl (100 ml). The reaction mixture was extracted with ether and the organic layer was washed with 2M HCl, NaHCO$_3$, brine, dried (MgSO$_4$). The solvent was removed by evaporation and the residue was chromatographed on a Biotage column eluting with ether-petroleum ether(40–60° C.) (1:9; 1:1) to give the title compound (16.99 g). ES+ve 250 (MH)$^+$.

x) (1R)-2-Amino-1-(2,2-dimethyl-4H-1,3-benzodioxin-6-yl)ethanol (1R)-2-Azido-1-(2,2-dimethyl-4H-1,3-benzodioxin-6-yl)ethanol (16.99 g) was hydrogenated over 10% Pd—C (1 g) in EtOH (300 ml). The catalyst was collected by filtration, and washed with EtOH. The combined washings were evaporated under reduced pressure and the residue was triturated in ether to give the title compound (5.86 g). The mother liquors were chromatographed on a Biotage column eluting with toluene:EtOH:aqueous ammonia (85:14:1) to give a further batch of the title compound (5.99 g). LCMS RT=1.68 min, ES+ve 206 (MH—H$_2$O)$^+$.

xi) 3-(3-{4-[(6-{[(2R)-2-(2,2-Dimethyl-4H-1,3-benzodioxin-6-yl)-2-hydroxyethyl]amino}hexyl)oxy] butyl}phenyl)imidazolidine-2,4-dione A solution of 6-{4-[3-(2,5-dioxoimidazolidin-1-yl)phenyl]butoxy}hexyl methanesulfonate (766 mg) in DMF (8 ml) was treated with tetrabutylammonium bromide (578 mg) and (1R)-2-amino-1-(2,2-dimethyl-4H-1,3-benzodioxin-6-yl)ethanol (544 mg) and the mixture was stirred at 20° C. for 3 d. The solvent was removed under reduced pressure, the residue was dissolved in $CH_2Cl_2$, washed with water and purified by chromatography on Biotage (40 g) eluting with 3% 2M $NH_3$ in MeOH:$CH_2Cl_2$ to give the title compound (417 mg). ES+ve 554 (MH)+.

xii) 3-[3-(4-{[6-({[(2R)-2-Hydroxy-2-[4-hydroxy-3-(hydroxymethyl)phenyl]ethyl}amino)hexyl]oxy}butyl)phenyl] imidazolidine-2,4-dione acetate A solution of 3-(3-{4-[(6-{[(2R)-2-(2,2-dimethyl-4H-1,3-benzodioxin-6-yl)-2-hydroxyethyl]amino}hexyl)oxy] butyl}phenyl)imidazolidine2,4-dione (414 mg) in acetic acid (20 ml) and water (5 ml) was heated to 75° C. for 30 min before evaporating to dryness. The residue was purified by chromatography on Biotage (40 g) eluting with $CH_2Cl_2$: MeOH:2M $NH_3$ in MeOH (85:10:5). Appropriate fractions were combined and evaporated to dryness. Acetone (10 ml) was added and the mixture was re-evaporated under reduced pressure to give the title compound (290 mg). LCMS RT=2.44 min, ES+ve 514 (MH)+.

1H NMR (DMSO+D2O) 7.36 (1H, t, J 8 Hz), 7.28 (1H, br s), 7.20 (1H, d, J 8 Hz), 7.10 (1H, s), 7.09 (1H, d, J 8 Hz), 7.04 (1H, dd, J 8, 2 Hz), 6.73 (1H, d, J 8 Hz), 4.73 (1H, dd, J 5, 8 Hz), 4.45 (2H, s), 4.08 (2H, s), 3.33 and 3.30 (2H each, t, J 7 Hz), 2.98–2.90 (2H, m), 2.86 (2H, t, J 7 Hz), 2.59 (2H, t, J 7 Hz), 1.85 (3H, s), 1.62–1.4 (8H, m), 1.3–1.2 (4H, m)

EXAMPLE 2

3-[3-(3-{[7-({(2R)-2-Hydroxy-2-[4-hydroxy-3-(hydroxymethyl)phenyl]ethyl}amino)heptyl] oxy}propyl)phenyl]imidazolidine-2,4-dione acetate i) 1-{3-[(7-Bromoheptyl)oxy]prop-1-ynyl}-3-nitrobenzene
was prepared using methods similar to those described in Example 1ii). tlc Rf 0.21 (5% $Et_2O$/petrol)

ii) 7-{[3-(3-Nitrophenyl)prop-2-ynyl]oxy}heptyl acetate
was prepared using methods similar to those described in Example 1iii). LCMS RT=3.78 min iii) 7-[3-(3-Aminophenyl)propoxy]heptyl acetate
was prepared using methods similar to those described in Example 1iv). LCMS RT=3.38 min iv) Ethyl N-({[3-(3-{[7-(acetyloxy)heptyl]oxy}propyl)phenyl]amino}carbonyl)glycinate
was prepared using methods similar to those described in Example 1v). LCMS RT=3.52 min v) 3-(3-{3-[(7-Hydroxyheptyl)oxy]propyl}phenyl)imidazolidine-2,4-dione
was prepared using methods similar to those described in Example 1vi). ES+ve 349 (MH)+.

vi) 7-{3-[3-(2,5-dioxoimidazolidin-1-yl)phenyl] propoxy}heptyl methanesulfonate was prepared using methods similar to those described in Example 1vii). ES+ve 427 (MH)+.

vii) 3-(3-{3-[(7-{[(2R)-2-(2,2-Dimethyl-4H-1,3-benzodioxin-6-yl)-2-hydroxyethyl]amino}heptyl)oxy] propyl}phenyl)imidazolidine-2,4-dione formate
was prepared using methods similar to those described in Example 1xi). ES+ve 554 (MH)+.

viii) 3-[3-(3-{[7-({(2R)-2-Hydroxy-2-[4-hydroxy-3-(hydroxymethyl)phenyl]ethyl}amino)heptyl]oxy}propyl)phenyl]imidazolidine-2,4-dione acetate
was prepared using methods similar to those described in Example 1xii). LCMS RT=2.39 min, ES+ve 514 (MH)+.

EXAMPLE 3

1-[3-(4-{[6-({(2R)-2-Hydroxy-2-[4-hydroxy-3-(hydroxymethyl)phenyl]ethyl}amino)hexyl]oxy}butyl) phenyl]imidazolidine-2-one acetate i) Di(tert-butyl)2-(2,2-dimethyl-4H-1,3-benzodioxin-6-yl)-2-oxoethylimidodicarbonate Caesium carbonate (70.4 g) was added to a stirred suspension of 2-bromo-1-(2,2-dimethyl-4H-1,3-benzodioxin-6-yl)ethanone, (Glaxo, DE 3513885, 1985) (61.8 g) and di-t-butyl iminodicarboxylate (47.15 g) in acetonitrile (600 ml) under nitrogen. After vigorous stirring at 21° for 24 h the mixture was diluted with water (ca800 ml) and the product was extracted with diethyl ether (1 litre, then 200 ml). The combined organic layers were washed with brine, dried ($MgSO_4$) and concentrated to ca400 ml. The white crystals were collected by filtration, washed with diethyl ether and dried to give the title compound (24.4 g) δ ($CDCl_3$) 7.78(1H, dd, J 8, 2 Hz), 7.65 (1H, brs), 6.87(1H, d, J 8 Hz), 4.97(2H, s), 4.88(2H, s), 1.56(6H, s) and 1.48(18H, s). Further concentration of the mother liquors gave additional product (13.8 g). A third crop (7.1 g) was obtained by chromatographing the mother liquors on silica gel, evaporating the appropriate eluate and triturating with diethyl ether.

ii) tert-Butyl 2-(2,2-dimethyl-4H-1,3-benzodioxin-6-yl)-2-oxoethylcarbamate

Trifluoroacetic acid (92 ml) was added to a stirred solution of di(tert-butyl) 2-(2,2-dimethyl-4H-1,3-benzodioxin-6-yl)-2-oxoethylimidodicarbonate, (352.55 g) in dichloromethane (3.6 litres) at 21° and the reaction was stirred for 1.5 h. Aqueous NaOH solution (1.75 litres) was added and after 10 min the phases were separated. The organic layer was washed with water, dried ($MgSO_4$) and evaporated to an oil. This was stored under high vacuum overnight and then triturated with hexane:ether (3:1) to give the crude product (226.61 g). This was purified by recrystallisation from diethyl ether to give the title compound (122.78 g). Further product (61.5 g) was obtained from the mother liquors by evaporation and chromatography on a Biotage using 15% ethyl acetate in hexane. LCMS RT=3.37 min.

iii) tert-Butyl (2R)-2-(2,2-dimethyl-4H-1,3-benzodioxin-6-yl)-2-hydroxyethylcarbamate A 2M solution of borane—dimethyl sulphide in THF (28 ml) was added slowly to a 1M solution of (R)-tetrahydro-1-methyl-3,3-diphenyl-1H,3H-pyrrolo[1,2-c][1,3,2]oxazaborole in toluene (56 ml) at 0° under nitrogen. A solution of tert-butyl 2-(2,2-dimethyl-4H-1,3-benzodioxin-6-yl)-2-oxoethylcarbamate, (108.2 g) in THF (1.3 litres) was added slowly keeping the temperature below 5° followed by 2M solution of borane—dimethyl sulphide in THF (252 ml) over 50 min. After 1 h, 2M HCl (170 ml) was added with cooling and the mixture was partitioned between ethyl acetate and water. The organic layer was washed with saturated $NaHCO_3$ solution and brine and dried (MgSO₄). The solution was concentrated and the product purified by chromatography on flash silica gel (800 g), eluting successively with hexane: ethyl acetate (4:1 then 3:1) to give the title compound (93.3 g), LCMS RT=3.31 min.

iv) (5R)-5-(2,2-Dimethyl-4H-1,3-benzodioxin-6-yl)-1,3-oxazolidin-2-one tert-Butyl (2R)-2-(2,2-dimethyl-4H-1,3-benzodioxin-6-yl)-2-hydroxyethylcarbamate, (86.37 g) in DMF (600 ml) was added dropwise to a stirred suspension of sodium hydride (60% oil dispersion, 11.9 g) in DMF (160 ml) with cooling such that the internal temperature remained at 0° under nitrogen. The mixture was stirred at 21° for 2 h. The mixture was recooled to 0° and 2M HCl (134 ml) was added. The mixture was diluted with water and the product was extracted with ethyl acetate twice. The solution was washed with brine twice, dried (MgSO₄) and evaporated to give the title compound (63.55 g) LCMS RT=2.66 min.

v) 6-Bromohexyl but-3-ynyl ether
was prepared as described in Example 1(i).

vi) (5R)-3-[6-(But-3-ynyloxy)hexyl]-5-(2,2-dimethyl-4H-1,3-benzodioxin-6-yl)-1,3-oxazolidin-2-one (5R)-5-(2,2-dimethyl-4H-1,3-benzodioxin-6-yl)-1,3-oxazolidin-2-one (10 g) in DMF (100 ml) was added dropwise to a stirred suspension of sodium hydride (60% oil dispersion, 2.33 g) in DMF (50 ml) with stirring under nitrogen and maintaining the internal temperature at 0°. Stirring was continued at 0–5° for 1 h. The mixture was recooled to 0° and a solution of 6-bromohexyl but-3-ynyl ether (14.7 g) in DMF (50 ml) was added over 1 min. The mixture was then stirred at 20–30° for 2 h. 2M HCl (9 ml) was added and the mixture was partitioned between water and diethyl ether. The aqueous layer was extracted with more diethyl ether and the combined organic layers were washed twice with brine. After drying (MgSO₄) the solution was concentrated and loaded onto a column of silica gel (600 g) set up in diethyl ether: petroleum ether (bp 40–60°) (1:2). The column was eluted successively with this mixture, then (1:1) and then diethyl ether to give the title compound (13.88 g) LCMS RT=3.45 min.

vii) 1-(3-Iodophenyl)imidazolidin-2-one
A solution of 3-iodoaniline (1 g) in CH₂Cl₂ (5 ml) and diisopropylethylamine (2 ml) was treated with 2-chloroethylisocyanate (0.4 ml) and the mixture was stirred at 20° C. for 3 d. The mixture was diluted with EtOAc and washed with 2M HCl, dried and evaporated to dryness. The residue was dissolved in DMF (5 ml), treated with sodium hydride (60% oil dispersion, 182 mg), and the mixture was stirred for 20 h under nitrogen. The mixture was diluted with EtOAc, washed with 2M HCl, brine, dried and evaporated to dryness. The residue was crystallised from hot EtOAc/MeOH. Trituration in Et₂O of the residue obtained by evaporation of the mother liquor gave the title compound (240 mg). LCMS RT=3.03 min.

viii) (5R)-5-(2,2-Dimethyl-4H-1,3-benzodioxin-6-yl)-3-[6-({4-[3-(2-oxoimidazolidin-1-yl)phenyl]but-3-ynyl}oxy)hexyl]-1,3-oxazolidin-2-one (5R)-3-[6-(But-3-ynyloxy)hexyl]-5-(2,2-dimethyl-4H-1,3-benzodioxin-6-yl)-1,3-oxazolidin-2-one (376 mg) was stirred with 1-(3-iodophenyl)imidazolidin-2-one (250 mg) in DMF (10 ml) and diisopropylethylamine (3 ml) under nitrogen for 10 min.

Dichlorobis(triphenylphosphine)palladium (30 mg) and cuprous iodide (8 mg) were added and the mixture was stirred for 17 h under nitrogen at 20° C. The mixture was evaporated to dryness and the residue was chromatographed on Biotage (40 g) eluting with EtOAc-petroleum ether (bp 40–60° C.) (1:1) and then on two preparative plates (20×20 cm) eluting with MeOH—CH₂Cl₂ (1:19) to give the title compound (120 mg). LCMS RT=3.49 min ix) (5R)-5-(2,2-Dimethyl-4H-1,3-benzodioxin-6-yl)-3-(6-{4-[3-(2-oxoimidazolidin-1-yl)phenyl]butoxyl{hexyl)-1,3-oxazolidin-2one (5R)-5-(2,2-Dimethyl-4H-1,3-benzodioxin-6-yl)-3-[6-({4-[3-(2-oxoimidazolidin-1-yl)phenyl]but-3-ynyl}oxy)hexyl]-1,3-oxazolidin-2-one (120 mg) was hydrogenated over platinum oxide (54 mg) in EtOH (100 ml). The catalyst was removed by filtration and the residue was leached with EtOH. The combined filtrates were evaporated under reduced pressure to give the title compound (113 mg). LCMS RT=3.55 min x) 1-(3-{4-[(6-{[(2R)-2-(2,2-Dimethyl-4H-1,3-benzodioxin-6-yl)-2-hydroxyethyl]amino}hexyl)oxy]butyl}phenyl)imidazolidin-2-one (5R)-5-(2,2-Dimethyl-4H-1,3-benzodioxin-6-yl)-3-(6-{4-[3-(2-oxoimidazolidin-1-yl)phenyl]butoxy}hexyl)-1,3-oxazolidin-2-one (113 mg) was stirred in THF (8 ml) while purging with a vigorous stream of nitrogen for 3 min. Potassium trimethylsilanolate (285 mg) was added and the mixture was stirred at 80° C. under nitrogen for 0.75 h. MeOH (10 ml) was added and then the solvents were removed under reduced pressure. The residue was dissolved in MeOH and applied to a silica Bond Elut cartridge (10 g) which was preconditioned in CH₂Cl₂ eluting with CH₂Cl₂, 5% MeOH—CH₂Cl₂, 2% increasing to 10% 2M NH₃ in MeOH—CH₂Cl₂ to give the title compound (39 mg). LCMS RT=2.94 min xi) 1-[3-(4-{[6-({(2R)-2-Hydroxy-2-[4-hydroxy-3-(hydroxymethyl)phenyl]ethyl}amino)hexyl]oxy}butyl)phenyl]imidazolidin-2-one acetate was prepared using methods similar to those described in Example 1xii). LCMS RT=2.47 min, ES+ve 500 (MH)⁺

EXAMPLE 4

1-[3-(4-{[6-({(2R)-2-Hydroxy-2-[4-hydroxy-3-(hydroxymethyl)phenyl]ethyl}amino)hexyl]oxy}butyl)phenyl]imidazolidine-2,4-dione formate i) 1-(3-Iodophenyl)imidazolidine-2,4-dione
A solution of 3-iodophenylurea (2.1 g) in DMF (20 ml) was treated with sodium hydride (60% oil dispersion; 640 mg), followed by ethyl chloroacetate (0.93 ml) and the mixture was stirred for 5 h. The mixture was partitioned between EtOAc and 2M HCl and the organic solution was washed with NaHCO₃, brine, dried and evaporated to dryness to give the title compound (2.08 g) ES+ve 303(MH)⁺.

ii) 1-{3-[4-({6-[(5R)-5-(2,2-Dimethyl-4H-1,3-benzodioxin-6-yl)-2-oxo-1,3-oxazolidin-3-yl]hexyl}oxy)but-1-ynyl]phenyl}imidazolidine-2,4-dione was prepared using methods similar to those described in Example 3vi). LCMS RT=3.63 min iii) 1-{3-[4-({6-[(5R)-5-(2,2-Dimethyl-4H-1,3-benzodioxin-6-yl)-2-oxo-1,3-oxazolidin-3-yl]hexyl}oxy)butyl]phenyl}imidazolidine-2,4-dione was prepared using methods similar to those described in Example 3vii). LCMS RT=3.53 min iv) 1-(3-{4-[(6-{[(2R)-2-(2,2-Dimethyl-4H-1,3-benzodioxin-6-yl)-2-hydroxyethyl]amino}hexyl)oxy]butyl}phenyl)imidazolidine-2,4-dione was prepared using methods similar to those described in Example 3viii). LCMS RT=2.98 min v) 1-[3-(4-{[6-({(2R)-2-Hydroxy-2-[4-hydroxy-3-(hydroxymethyl)phenyl]ethyl}amino)hexyl]oxy}butyl)phenyl]imidazolidine-2,4-dione formate was prepared using methods similar to those described in Example 1xii). The crude product was purified on HPLC eluting with a gradient of MeCN—H$_2$O—HCO$_2$H to give the title compound. LCMS RT=2.53 min, ES+ve 514 (MH)$^+$.

EXAMPLE 5

3-[3-(4-{[6-({(2R)-2-Hydroxy-2-[4-hydroxy-3-(hydroxymethyl)phenyl]ethyl}amino)hexyl]oxy}butyl)phenyl]imidazolidine-2,4-dione acetate i) Ethyl N-{[(3-iodophenyl)amino]carbonyl}glycinate A solution of 3-iodoaniline (9.39 g) in dichloromethane (75 ml) was treated with ethyl isocyanatoacetate (7.21 ml) at 0° C. and the mixture was stirred for 2 h and allowed to warm to 20° C. EtOH (10 ml) was added and the mixture was stirred for 15 h. The solvents were evaporated under reduced pressure and the residue was triturated in Et$_2$O to give the title compound (12.9 g)LCMS RT=3.08 min.

ii) 3-(3-Iodophenyl)imidazolidine-2,4-dione

A solution of ethyl N-{[(3-iodophenyl)amino]carbonyl}glycinate (9.42 g) in DMF (60 ml) was treated with sodium hydride (60% oil dispersion, 1.2 g) at 20° C. After 2 h the reaction mixture was treated with aqueous 2M HCl (200 ml) and stirred overnight. The solid was collected by filtration, washed with water and dried to give the title compound (6.9 g) LCMS RT=2.45 min.

iii) 3-(3-{4-[(6-Bromohexyl)oxy]but-1-ynyl}phenyl)imidazolidine-2,4-dione

A mixture of 3-(3-iodophenyl)imidazolidine-2,4-dione (0.75 g), 6-bromohexyl but-3-ynyl ether (1.3 g), bis(triphenylphosphine)palladium dichloride (87 mg) in DMF (10 ml) was treated with diisopropylethylamine (3 ml) and copper (I) iodide (23 mg) and the mixture was stirred for under nitrogen for 24 h. The solvents were removed under reduced pressure, the residue was diluted with EtOAc and washed with aqueous 2M HCl, aqueous dilute ammonia, brine and dried (MgSO$_4$). The solvent was removed under reduced pressure and the residue was purified on two Bond Elut 10 g silica cartridges eluting with dichloromethane, Et$_2$O, and EtOAc to give the title compound (760 mg) together with 3-(3-{4-[(6-iodohexyl)oxy]but-1-ynyl}phenyl)imidazolidine-2,4-dione (760 mg, 22:3).

iv) 3-(3-{4-[(6-{[(2R)-2-(2,2-Dimethyl-4H-1,3-benzodioxin-6-yl)-2-hydroxyethyl]amino}hexyl)oxy]but-1-ynyl}phenyl)imidazolidine-2,4-dione A mixture of 3-(3-{4-[(6-bromohexyl)oxy]but-1-ynyl}phenyl)imidazolidine-2,4-dione and 3-(3-{4-[(6-iodohexyl)oxy]but-1-ynyl}phenyl)imidazolidine-2,4-dione (760 mg, 22:3), (1R)-2-amino-1-(2,2-dimethyl-4H-1,3-benzodioxin-6-yl)ethanol (800 mg) in DMF (5 ml) was stirred at 20° C. for 22 h. The solvent was removed under reduced pressure and the residue was diluted with EtOAc and washed with water, brine and dried (MgSO$_4$). The solution was concentrated and purified by chromatography on Biotage (40 g) eluting with dichloromethane:MeOH:1M ammonia in methanol (98:1:1 to 95:4:1) to give the title compound (368 mg) LCMS RT=2.59 min.

v) 3-(3-{4-[(6-{[(2R)-2-(2,2-Dimethyl-4H-1,3-benzodioxin-6-yl)-2-hydroxyethyl]amino}hexyl)oxy]butyl}imidazolidine-2,4-dione A solution of 3-(3-{4-[(6-{[(2R)-2-(2,2-Dimethyl-4H-1,3-benzodioxin-6-yl)-2-hydroxyethyl]amino}hexyl)oxy]but-1-ynyl}phenyl)imidazolidine-2,4-dione (368 mg) was hydrogenated over platinum oxide (100 mg) in EtOAc (100 ml) over 3 h. The catalyst was collected by filtration, washed with EtOAc and EtOH. The combined filtrate and washings were evaporated under reduced pressure to give the title compound LCMS RT=2.55 min vi) 3-[3-(4-{[6-({(2R)-2-Hydroxy-2-[4-hydroxy-3-(hydroxymethyl)phenyl]ethyl}amino)hexyl]oxy}butyl)phenyl]imidazolidine-2,4-dione acetate was prepared using methods similar to those described in Example 1xii LCMS RT=2.38 min, ES+ve 514(MH)$^+$.

EXAMPLE 6

3-[3-(4-{[6-({(2R)-2-Hydroxy-2-[4-hydroxy-3-(hydroxymethyl)phenyl]ethyl}amino)hexyl]oxy}butyl)phenyl]imidazolidine-2,4-dione acetate (i) (1R) 2-Bromo-1-(2,2-dimethyl-4H-1,3-benzodioxin-6-yl)ethanol A solution R-diphenylprolinol (75 mg) in THF (2 ml) was treated with borane-THF (1M, 20.5 ml) over 20 min at 20° C. under nitrogen. After the addition was complete the solution was kept between 30 and 35° C. for 1 h and then cooled in ice and 2-bromo-1-(2,2-dimethyl-4H-1,3-benzodioxin-6-yl)ethanone (DE3513885) (3.9 g) in THF (10 ml) was added over 1.5 h keeping the temperature below 5° C. The mixture was stirred under nitrogen for a further 0.5 h and then methanol (4 ml) was added at 0° C. The solvent was removed under reduced pressure and the residue was purified by chromatography on flash silica gel eluting with ethyl acetate-cyclohexane (1:4) to give the title compound (3.31 g) δ (CDCl$_3$) 7.15 (1H, dd, J 8, 2 Hz), 7.03 (1H, br s), 6.82 (1H, d, J 8 Hz), 4.85 (3H, s and m), 3.61 (1H, dd, J 10, 4 Hz), 3.50 (1H, dd, J 10, 9 Hz), 1.54 (6H, s).

(ii) {[(1R)-2-Bromo-1-(2,2-dimethyl-4H-1,3-benzodioxin-6-yl)ethyl]oxy}(triethyl)silane Triethylsilyl chloride (205 g) was added dropwise to a stirred mixture of (1R)-2-Bromo-1-(2,2-dimethyl-4H-1,3-benzodioxin-6-yl)ethanol (350 g) and imidazole (108.5 g) in DMF (875 ml) at 5° C. Upon complete addition the mixture was warmed to 15° C. and stirred, at this temperature for 1 h. n-Hexane (3500 ml) was then added to the mixture which was washed with water (3×1750 ml). The organic layer was dried over anhydrous MgSO$_4$ before being filtered and concentrated under reduced pressure to give the title compound (488.6 g) as an oil, δ (DMSO-d$_6$) 7.18 (1H, d, J 8.2 Hz), 7.10 (1H, s), 6.75 (1H, d, J 8.2 Hz), 4.83 (1H, m), 4.78 (2H, d, J 6.9 Hz), 3.55 (2H, m), 1.45 (6H, s), 0.84 (9H, t, J 8.1 Hz), 0.51 (6H, m).

iii) N-Benzyl-N-{(2R)-2-(2,2-dimethyl-4H-1,3-benzodioxin-6-yl)-2-[(triethylsilyl)oxy]ethyl}amine A mixture of {[(1R)-2-bromo-1-(2,2-dimethyl-4H-1,3-benzodioxin-6-yl)ethyl]oxy}(triethyl)silane (130 g) and benzylamine (177 ml) in 1,4-dioxane (650 ml) was heated at 105° C. with stirring overnight. The mixture was then cooled to room temperature and water (150 ml) and diethyl ether (1200 ml) added. The layers were separated and the ethereal layer was washed with saturated ammonium chloride solution (3×600 ml), saturated sodium bicarbonate solution (200 ml) and then brine (200 ml). The solution was dried over anhydrous $Na_2SO_4$ before being filtered and concentrated under reduced pressure to give the title compound (129.9 g) as an oil, δ (CDCl$_3$) 7.22 (5H, m), 7.02 (1H, d, J 8.7 Hz), 6.86 (1H, s), 6.68 (1H, d, J 8.3 Hz), 4.75 (2H, s), 4.69 (1H, m), 3.73 (2H, s), 2.70 (2H, m), 1.46 (6H, s), 0.79 (9H, m), 0.44 (6H, m).

iv) (1R)-2-(Benzylamino)-1-(2,2-dimethyl-4H-1,3-benzodioxin-6-yl)ethanol

Tetrabutylammonium fluoride (395 ml, 1M in THF) was added dropwise to a stirred solution of N-benzyl-N-{(2R)-2-(2,2-dimethyl-4H-1,3-benzodioxin-6-yl)-2-[(triethylsilyl)oxy]ethyl}amine (129.9 g) in THF (900 ml) at 5° C. Upon complete addition the reaction mixture was maintained at this temperature for 15 min before water (600 ml) was added. The resulting slurry was diluted with diethyl ether (500 ml) and filtered. The filtrate was washed with water (2×500 ml) and brine (500 ml) before being dried over anhydrous $Na_2SO_4$. The resulting mixture was filtered and concentrated under reduced pressure to give a solid which was triturated with diisopropyl ether to give the title compound (70 g) as a solid, δ (CDCl$_3$) 7.31 (5H, m), 7.09 (1H, d, J 8 Hz), 6.98 (1H, s), 6.77 (1H, d J 8 Hz), 4.82 (2H, s), 4.63 (1H, m), 3.83 (2H, d, J 4 Hz), 2.80 (2H, m), 1.52 (6H, s).

v) 3-(3-{4-[(6-{Benzyl[(2R)-2-(2,2-dimethyl-4H-1,3-benzodioxin-6-yl)-2-hydroxyethyl]amino}hexyl)oxy]but-1-ynyl}phenyl)imidazolidine-2,4-dione A solution of 3-(3-{4-[(6-bromohexyl)oxy]but-1-ynyl}phenyl)imidazolidine-2,4-dione and 3-(3-{4-[(6-iodohexyl)oxy]but-1-ynyl}phenyl)imidazolidine-2,4-dione (3:1, 23.98 g) in acetonitrile (240 ml) and diisopropylethylamine (20 ml) was treated with (1R)-2-(benzylamino)-1-(2,2-dimethyl-4H-1,3-benzodioxin-6-yl)ethanol (18.22 g) and the mixture was heated to 50° C. for 5 days. The solvent was removed under reduced pressure, the residue was diluted with EtOAc (250 ml) and washed with water. The aqueous phase was re-extracted with EtOAc (75 ml) and the combined organic solutions were washed with brine, dried (MgSO$_4$), and evaporated. The residue was purified by chromatography on flash silica gel eluting with dichloromethane-EtOAc (1:1) to give the title compound (17.25 g) LCMS RT=2.80 min vi) 3-[3-(4-{[6-([(2R)-2-Hydroxy-2-[4-hydroxy-3-(hydroxymethyl)phenyl]ethyl}amino)hexyl]oxy}butyl)phenyl]imidazolidine-2,4-dione A solution of 3-(3-{4-[(6-{benzyl[(2R)-2-(2,2-dimethyl-4H-1,3-benzodioxin-6yl)-2-hydroxyethyl]amino}hexyl)oxy]but-1-ynyl}phenyl)imidazolidine-2,4-dione (9.05 g) in a mixture of isopropanol-EtOAc (9:1, 200 ml) was hydrogenated over Pearlman's catalyst (1.8 g). After 2 days aqueous 2M HCl (10 ml) was added and the mixture was hydrogenated for a further 2 h. The catalyst was removed by filtration and the filtrate was concentrated under reduced pressure. The residue was purified by chromatography on Biotage eluting with dichloromethane-isopropanol-880 ammonia (34:7:1) to give the title compound (2.8 g) LCMS RT=2.34 min ES+ve 514 (MH)$^+$.

EXAMPLE 7

3-[3-(4-{[6-([(2R)-2-Hydroxy-2-[4-hydroxy-3-(hydroxymethyl)phenyl]ethyl}amino)hexyl]oxy}butyl)phenyl]imidazolidine-2,4-dione acetate i) 6-(But-3-ynyloxy)hexanal 6-Bromohexylbut-3-ynyl ether (525 mg) in DMSO (2 ml) was added to a mixture of sodium bicarbonate (1 g) in DMSO (8 ml) at 150° C. with vigorous stirring and nitrogen bubbling through the solution. The mixture was stirred for 20 min at 150° C. and then allowed to cool to room temperature, diluted with Et$_2$O and washed with water. The aqueous layer was extracted with Et$_2$O and the combined ether layers were washed with dilute hydrochloric acid, brine, dried (MgSO$_4$) and evaporated to dryness to give the title compound (325 mg): IR 1726 cm$^{-1}$ MS(TSP+ve) m/z 186 (M+MH$_4$)$^+$.

ii) (1R)-2-{[6-(But-3-ynyloxy)hexyl][(1S)-2-hydroxy-1-phenylethyl]amino}-1-(2,2-dimethyl-4H-1,3-benzodioxin-6-yl)ethanol A mixture of 6-(but-3-ynyloxy)hexanal (434 mg) and (1R)-1-(2,2-dimethyl-4H-1,3-benzodioxin-6-yl)-2-{[(1S)-2-hydroxy-1-phenylethyl]amino}ethanol (WO0196278 A2) (710 mg) in chloroform (10 ml) was treated at 20° C. with sodium triacetoxyborohydride (866 mg) and stirred under nitrogen for 2 days. The mixture was diluted with EtOAc and aqueous sodium bicarbonate solution. The organic phase was separated and washed with sodium bicarbonate solution, brine, dried and purified on a silica Bond Elut cartridge (10 g) eluting with dichloromethane, Et$_2$O and finally EtOAc to give the title compound (810 mg): LCMS RT=2.69 min, ES+ve m/z 496 (M+H)$^+$.

iii) 3-(3-{4-[(6-{[(2R)-2-(2,2-dimethyl-4H-1,3-benzodioxin-6-yl)-2-hydroxyethyl][(1S)-2-hydroxy-1-phenylethyl]amino}hexyl)oxy]but-1-ynyl}phenyl)imidazolidine-2,4-dione was prepared using methods similar to those described in Example 1ii LCMS RT=2.82 min, ES+ve 670 (MH)$^+$.

iv) 3-[3-(4-{[6-([(2R)-2-Hydroxy-2-[4-hydroxy-3-(hydroxymethyl)phenyl]ethyl}amino)hexyl]oxy}butyl)phenyl]imidazolidine-2,4-dione was prepared using methods similar to those described in Example 6(vi) LCMS RT=2.39 min, ES+ve 514 (MH)$^+$.

EXAMPLE 8

3-[3-(4-{[6-({(2S)-2-Hydroxy-2-[4-hydroxy-3-(hydroxymethyl)phenyl]ethyl}amino)hexyl]oxy}butyl)phenyl]imidazolidine-2,4-dione acetate i) 3-(3-{4-[(6-{[(2S)-2-(2,2-Dimethyl-4H-1,3-benzodioxin-6-yl)-2-hydroxyethyl]amino}hexyl)oxy]but-1-ynyl}phenyl)imidazolidine-2,4-dione was prepared using methods similar to those described in Example 5iv from (1S)-2-amino-1-(2,2-dimethyl-4H-1,3-benzodioxin-6-yl)ethanol (*Tetrahedron:Asymmetry* 2001, 12, 2005).

ii) 3-(3-{4-[(6-{[(2S)-2-(2,2-Dimethyl-4H-1,3-benzodioxin-6-yl)-2-hydroxyethyl]amino}hexyl)oxy]butyl}phenyl)imidazolidine-2,4-dione was prepared using methods similar to those described in Example 5v.

iii) 3-[3-(4-{[6-({(2S)-2-Hydroxy-2-[4-hydroxy-3-(hydroxymethyl)phenyl]ethyl}amino)hexyl]oxy}butyl)phenyl]imidazolidine-2,4-dione acetate was prepared using methods similar to those described in Example 1xii.

EXAMPLE 9

3-[4-(4-{[6-({(2R)-2-Hydroxy-2-[4-hydroxy-3-(hydroxymethyl)phenyl]ethyl}amino)hexyl]oxy}butyl)phenyl]imidazolidine-2,4-dione acetate i) Ethyl N-{[(4-iodophenyl)amino]carbonyl}glycinate was prepared using method similar to those described in Example 5i. LCMS RT=3.1 min.

ii) 3-(4-Iodophenyl)imidazolidine-2,4-dione was prepared using method similar to those described in Example 5ii. LCMS RT=2.49 min.

iii) 3-(4-{4-[(6-Bromohexyl)oxy]but-1-ynyl}phenyl)imidazolidine-2,4-dione was prepared using method similar to those described in Example 5iii. LCMS RT=3.46 min.

iv) 3-(4-{4-[(6-{[(2R-2-(2,2-Dimethyl-4H-1,3-benzodioxin-6-yl)-2-hydroxyethyl]amino}hexyl)oxy]but-1-ynyl}phenyl)imidazolidine-2,4-dione was prepared using method similar to those described in Example 5iv. LCMS RT=2.58 min.

v) 3-(4-{4-[(6-{[(2R)-2-(2,2-Dimethyl-4H-1,3-benzodioxin-6-yl)-2-hydroxyethyl]amino}hexyl)oxy]butyl}phenyl)imidazolidine-2,4-dione was prepared using method similar to those described in Example 5v. LCMS RT=2.55 min.

vi) 3-[4-(4-{[6-({(2R)-2-Hydroxy-2-[4-hydroxy-3-(hydroxymethyl)phenyl]ethyl}amino)hexyl]oxy}butyl)phenyl]imidazolidine-2,4-dione acetate was prepared using method similar to those described in Example 1xii. LCMS RT=2.34 min, ES+ve 514(MH)+.

EXAMPLE 10

3-[2-(4-{[6-({(2R)-2-Hydroxy-2-[4-hydroxy-3-(hydroxymethyl)phenyl]ethyl}amino)hexyl]oxy}butyl)phenyl]imidazolidine-2,4-dione acetate i) Ethyl N-{[(2-iodophenyl)amino]carbonyl}glycinate was prepared using method similar to those described in Example 5i. LCMS RT=2.62 min.

ii) 3-(2-Iodophenyl)imidazolidine-2,4-dione

A solution of ethyl N-{[(2-iodophenyl)amino]carbonyl}glycinate (6 g) in MeOH was treated with aqueous NaOH (2M, 17.5 ml) and stirred under nitrogen for 0.5 h at 20° C. The reaction mixture was quenched by adding aqueous 2M HCl (20 ml) and water. The white solid obtained was collected by filtration and then was dissolved in dioxane (30 ml) and treated with p-toluenesulfonic acid (750 mg). The mixture was heated and stirred at 100° C. for 16 h. The solvent was removed under reduced pressure, the residue was diluted in EtOAc and washed with water, brine and dried (MgSO$_4$). The solvent was removed under reduced pressure and the residue was purified by chromatography on Biotage (40 g) eluting with dichloromethane:EtOAc (95:5 to 85:15) to give the title compound (1.68 g). LCMS RT=2.07 min.

iii) 3-(2-{4-[(6-Bromohexyl)oxy]but-1-ynyl}phenyl)imidazolidine-2,4-dione was prepared using methods similar to those described in Example 5iii. LCMS RT=3.29 min.

iv) 3-(2-{4-[(6-{[(2R)-2-(2,2-Dimethyl-4H-1,3-benzodioxin-6-yl)-2-hydroxyethyl]amino}hexyl)oxy]but-1-ynyl}phenyl)imidazolidine-2,4-dione was prepared using method similar to those described in Example 5iv. LCMS RT=2.48 min.

v) 3-(2-{4-[(6-{[(2R)-2-(2,2-Dimethyl-4H-1,3-benzodioxin-6-yl)-2-hydroxyethyl]amino}hexyl)oxy]butyl}phenyl)imidazolidine-2,4-dione was prepared using methods similar to those described in Example 5v. LCMS RT=2.42 min.

vi) 3-[2-(4-{[6-({(2R)-2-Hydroxy-2-[4-hydroxy-3-(hydroxymethyl)phenyl]ethyl}amino)hexyl]oxy}butyl)phenyl]imidazolidine-2,4-dione acetate was prepared using method similar to those described in Example 1xii. LCMS RT=2.08 min, ES+ve 514(MH)+.

EXAMPLE 11

3-[3-(4-{[6-({(2R)-2-Hydroxy-2-[4-hydroxy-3-(hydroxymethyl)phenyl]ethyl}amino)hexyl]oxy}butyl)benzyl]imidazolidine-2,4-dione acetate i) Ethyl N-{[(3-iodobenzyl)amino]carbonyl}glycinate was prepared using methods similar to those described in Example 5i. LCMS RT=2.71 min.

ii) 3-(3-Iodobenzyl)imidazolidine-2,4-dione

A solution of ethyl N-{[(3-iodobenzyl)amino]carbonyl}glycinate (7.6 g) in MeOH (40 ml) was treated with aqueous 2M NaOH (21.2 ml) and stirred under nitrogen at 20° C. The mixture crushed out instantly and was quenched by adding aqueous 2M HCl (22 ml). The residue was filtered to give the title compound (4.4 g) LCMS=2.73 min.

iii) 3-(3-{4-[(6-Bromohexyl)oxy]but-1-ynyl}benzyl)imidazolidine-2,4-dione was prepared using methods similar to those described in Example 5iii. LCMS RT=3.35 min.

iv) 3-(3-{4-[(6-{[(2R)-2-(2,2-Dimethyl-4H-1,3-benzodioxin-6-yl)-2-hydroxyethyl]amino}hexyl)oxy]but-1-ynyl}benzyl)imidazolidine-2,4-dione was prepared using method similar to those described in Example 5iv. LCMS RT=2.52 min.

v) 3-(3-{4-[(6-{[(2R)-2-(2,2-Dimethyl-4H-1,3-benzodioxin-6-yl)-2-hydroxyethyl]amino}hexyl)oxy]butyl}benzyl)imidazolidine-2,4-dione was prepared using method similar to those described in Example 5v. LCMS RT=2.70 min.

vi) 3-[3-(4-{[6-({(2R)-2-Hydroxy-2-[4-hydroxy-3-(hydroxymethyl)phenyl]ethyl}amino)hexyl]oxy}butyl)benzyl]imidazolidine-2,4-dione acetate was prepared using method similar to those described in Example 1xii. LCMS RT=2.44 min, ES+ve 528(MH)+.

EXAMPLE 12

3-[3-(5-{[5-({(2R)-2-Hydroxy-2-[4-hydroxy-3-(hydroxymethyl)phenyl]ethyl}amino)pentyl]oxy}pentyl)phenyl]imidazolidine-2,4-dione acetate i) 5-[(5-Bromopentyl)oxy]pent-1-yne
was prepared using methods similar to those described in Example 1i. LCMS RT=3.62 min.

ii) 5-Bromopentyl 5-(3-nitrophenyl)pent-4-ynyl ether
was prepared using methods similar to those described in Example 1ii. TLC Rf=0.18 (Et$_2$O-petroleum ether 1:19)

iii) 5-{[5-(3-Nitrophenyl)pent-4-ynyl]oxy}pentyl acetate
was prepared using methods similar to those described in Example 1iii. LCMS RT=3.69 min iv) 5-{[5-(3-Aminophenyl)pentyl]oxy}pentyl acetate
was prepared using methods similar to those described in Example 1iv. LCMS RT=3.12 min v) Ethyl N-({[3-(5-{[5-(acetyloxy)pentyl]oxy}pentyl)phenyl]amino}carbonyl)glycinate
was prepared using methods similar to those described in Example 1v. LCMS RT=3.45 min vi) 3-(3-{5-[(5-(Hydroxypentyl)oxy]pentyl}phenyl)imidazolidine-2,4-dione
was prepared using methods similar to those described in Example 1vi. LCMS RT=2.77 min vii) 5-[(5-{3-[3-(2,5-Dioxoimidazolidin-1-yl)phenyl}pentyl)oxy]pentyl methanesulfonate
was prepared using methods similar to those described in Example 1vii. LCMS RT=3.05 min viii) 3-(3-{5-[(5-Bromopentyl)oxy]pentyl}phenyl)imidazolidine-2,4-dione
A solution of 5-[(5-{3-[3-(2,5-dioxoimidazolidin-1-yl)]phenyl}pentyl)oxy]pentyl methanesulfonate (1.72 g) in acetonitrile (30 ml) was treated with tetrabutylammonium bromide (2.6 g) at 20° C. After two days more tetrabutylammonium bromide (1 g) was added and the mixture was stirred for a further day. The solvent was removed under reduced pressure and the residue was purified by chromatography on a Biotage cartridge (40 g) eluting with EtOAc-petroleum ether (1:2, 1:1) to give the title compound (754 mg) LCMS RT=3.36 min ix) 3-(3-{5-[(5-{[(2R)-2-(2,2-Dimethyl-4H-1,3-benzodioxin-6-yl)-2-hydroxyethyl]amino}pentyl)oxy]pentyl}phenyl)imidazolidine-2,4-dione
was prepared using methods similar to those described in Example 1xi LCMS RT=2.48 min x) 3-[3-(5-{[5-({(2R)-2-Hydroxy-2-[4-hydroxy-3-(hydroxymethyl)phenyl]ethyl}amino)pentyl]oxy}pentyl)phenyl]imidazolidine-2,4-dione acetate
was prepared using methods similar to those described in Example 1xii LCMS RT=2.22 min, ES+ve 514 (MH)$^+$.

EXAMPLE 13

3-[3-(5-{[6-({}(2R)-2-Hydroxy-2-[4-hydroxy-3-(hydroxymethyl)phenyl]ethyl}amino)hexyl]oxy}pentyl)phenyl]imidazolidine-2,4-dione acetate i) 5-[(6-Bromohexyl)oxy]pent-1-yne
was prepared using methods similar to those described in Example 1i. GCMS RT=5.6 min ii) 3-(3-{5-[(6Bromohexyl)oxy]pent-1-ynyl}phenyl)imidazolidine-2,4-dione
was prepared using methods similar to those described in Example 5iii LCMS RT=3.57 min iii) 3-(3-{5-[(6-{[(2R)-2-(2,2-Dimethyl-4H-1,3-benzodioxin-6yl)-2-hydroxyethyl]amino}hexyl)oxy]pent-1-ynyl}phenyl)imidazolidine-2,4-dione
was prepared using methods similar to those described in Example 5iv LCMS RT=2.54 min iv) 3-(3-{5-[(6-{[(2R)-2-(2,2-Dimethyl-4H-1,3-benzodioxin-6-yl)-2-hydroxyethyl]amino}hexyl)oxy]pentyl}phenyl)imidazolidine-2,4-dione
was prepared using methods similar to those described in Example 5v LCMS RT=2.71 min v) 3-[3-(5-{[6-({(2R)-2-Hydroxy-2-[4-hydroxy-3-(hydroxymethyl)phenyl]ethyl}amino)hexyl]oxy}pentyl)phenyl]imidazolidine-2,4-dione acetate
was prepared using methods similar to those described in Example 1xii LCMS RT=2.47 min, ES+ve 528 (MH)$^+$.

EXAMPLE 14

3-[3-(6-{[6-({(2R)-2-Hydroxy-2-[4-hydroxy-3-(hydroxymethyl)phenyl]ethyl}amino)hexyl]oxy}hexyl)phenyl]imidazolidine-2,4-dione acetate i) 6-[(6-Bromohexyl)oxy]hex-1-yne
was prepared using methods similar to those described in Example 1i. GCMS RT=5.99 min ii) 3-(3-Iodophenyl)imidazolidine-2,4-dione
was prepared using method similar to those described in Example 5ii. LCMS RT=2.54 min.

iii) 3-(3-{6-[(6-Bromohexyl)oxy]hex-1-ynyl}phenyl)imidazolidine-2,4-dione
was prepared using methods similar to those described in Example 5iii. LCMS RT=3.55 min.

iv) 3-(3-{6-[(6-{[(2R)-2-(2,2-Dimethyl-4H-1,3-benzodioxin-6-yl)-2-hydroxyethyl]amino}hexyl)oxy]hex-1-ynyl}phenyl)imidazolidine-2,4-dione
was prepared using method similar to those described in Example 5iv. LCMS RT=2.68 min.

v) 3-(3-{6-[(6-{[(2R)-2-(2,2-Dimethyl-4H-1,3-benzodioxin-6-yl)-2-hydroxyethyl]amino}hexyl)oxy]hexyl}phenyl)imidazolidine-2,4-dione
was prepared using method similar to those described in Example 5v. LCMS RT=2.73 min.

vi) 3-[3-(6-{[6-({(2R)-2-Hydroxy-2-[4-hydroxy-3-(hydroxymethyl)phenyl]ethyl}amino)hexyl]oxy}hexyl)phenyl]imidazolidine-2,4-dione acetate
was prepared using method similar to those described in Example 1xii. LCMS RT=2.81 min, ES+ve 582(MH)$^+$.

EXAMPLE 15

(5R)-5-[3-(4-{[6-({(2R)-2-Hydroxy-2-[4-hydroxy-3-(hydroxymethyl)phenyl]ethyl}amino)hexyl]oxy}butyl)benzyl]-5-methylimidazolidine-2,4-dione acetate i) Benzyl (2S,4R)-4-(3-iodobenzyl)-4-methyl-5-oxo-2-phenyl-1,3-oxazolidine-3-carboxylate A solution of benzyl (2S,4S)-4-methyl-5-oxo-2-phenyl-1,3-oxazolidine-3-carboxylate (*J. Org. Chem.* 2001, 66, 1903) (1.2 g) and 3-iodobenzyl bromide (1.15 g) in THF (8 ml) was added dropwise to a solution of lithium hexamethyldisilazane in THF (1M, 4.1 ml) diluted in THF (32 ml) at −30° C. The mixture was stirred at this temperature and then allowed to warm to 20° C. over 4 h. Aqueous sodium bicarbonate solution was then added and the mixture was extracted with Et$_2$O. The organic phase was separated and dried (MgSO$_4$), filtered and evaporated. The residue was purified by chromatography on a Biotage cartridge (40 g) eluting with EtOAc-petroleum ether (1:9, 1:4) to give the title compound (1.48 g) HPLC RT=9.33 min.

ii) 3-Iodo-α-methyl-D-phenylalanine

A mixture of benzyl (2S,4R)-4-(3-iodobenzyl)-4-methyl-5-oxo-2-phenyl-1,3-oxazolidine-3-carboxylate (1.47 g) and potassium trimethylsilanolate (1.2 g) was suspended in THF (50 ml) and heated to 75° C. for 2.5 h. MeOH (10 ml) was added and the solvents were removed under reduced pressure. The residue was dissolved in MeOH and applied to two 10 g SCX-2 cartridges eluting with MeOH and then with 0.2M ammonia in MeOH. The ammoniacal solutions were evaporated to dryness to give the title compound (910 mg) LCMS RT=1.93 min.

iii) Methyl 3-iodo-α-methyl-D-phenylalaninate

A solution of 3-iodo-α-methyl-D-phenylalanine (0.9 g) in MeOH (50 ml) was treated with thionyl chloride (3.5 ml) and the mixture was heated to reflux for 3 days. The solvent was removed under reduced pressure and the residue was dissolved in EtOAc and washed with aqueous sodium bicarbonate, brine, dried (MgSO$_4$) and evaporated to dryness to give the title compound (0.73 g) LCMS RT=2.12 min.

iv) Methyl N-(aminocarbonyl)-3-iodo-α-methyl-D-phenylalaninate

A mixture of methyl 3-iodo-α-methyl-D-phenylalaninate (0.73 g) in acetic acid (3 ml) and water (1 ml) was treated with sodium cyanate (0.4 g) and stirred for 2 days at 20° C. The solvents were removed under reduced pressure and the residue was diluted with EtOAc. The solution was washed with water, brine, dried (MgSO$_4$) and evaporated to give the title compound (0.82 g) LCMS RT=2.74 min.

v) (5R)-5-(3-Iodobenzyl)-5-methylimidazolidine-2,4-dione

A mixture of methyl N-(aminocarbonyl)-3-iodo-α-methyl-D-phenylalaninate (0.82 g) and potassium carbonate (624 mg) in dimethyl sulfoxide (5 ml) was heated to 110° C. for 3 h and then allowed to cool to 20° C. overnight. The mixture was diluted with EtOAc and washed with 2M HCl, brine, dried (MgSO$_4$) and evaporated to dryness to give the title compound (521 mg) LCMS RT=2.61 min vi) (5R)-5-(3-{4-[(6-Bromohexyl)oxy]but-1-ynyl}benzyl)-5-methylimidazolidine-2,4-dione was prepared using methods similar to those described in Example 5iii LCMS RT=3.36 min vii) (5R)-5-(3-{4-[(6-{[(2R)-2-(2,2-Dimethyl-4H-1,3-benzodioxin-6-yl)-2-hydroxyethyl]amino}hexyl)oxy]but-1-ynyl}benzyl)-5-methylimidazolidine-2,4-dione was prepared using methods similar to those described in Example 5iv LCMS RT=2.58 min viii) (5R)-5-(3-{4-[(6-{[(2R)-2-(2,2-Dimethyl-4H-1,3-benzodioxin-6-yl)-2-hydroxyethyl]amino}hexyl)oxy]butyl}benzyl)-5-methylimidazolidine-2,4-dione was prepared using methods similar to those described in Example 5v LCMS RT=2.69 min ix) (5R)-5-[3-(4-{[6-({(2R)-2-Hydroxy-2-[4-hydroxy-3-(hydroxymethyl)phenyl]ethyl}amino)hexyl]oxy}butyl)benzyl]-5-methylimidazolidine-2,4-dione acetate was prepared using methods similar to those described in Example 1xii LCMS RT=2.41 min, ES+ve 542(MH)$^+$.

EXAMPLE 16

(5S)-5-[3-(4-{[6-({(2R)-2-Hydroxy-2-[4-hydroxy-3-(hydroxymethyl)phenyl]ethyl}amino)hexyl]oxy}butyl)benzyl]-5-methylimidazolidine2,4-dione acetate i) Benzyl (2R,4S)-4-(3-iodobenzyl)-4-methyl-5-oxo-2-phenyl-1,3-oxazolidine-3-carboxylate was prepared using methods similar to those described in Example 15i LCMS RT=3.98 min ii) 3-Iodo-α-methyl-L-phenylalanine was prepared using methods similar to those described in Example 15ii LCMS RT=2.03 min iii) Methyl 3-iodo-α-methyl-L-phenylalaninate was prepared using methods similar to those described in Example 15iii LCMS RT=2.21 min iv) Methyl N-(aminocarbonyl)-3-Iodo-α-methyl-L-phenylalaninate was prepared using methods similar to those described in Example 15iv LCMS RT=2.78 min v) (5S)-5-(3-Iodobenzyl)-5-methylimidazolidine-2,4-dione was prepared using methods similar to those described in Example 15v LCMS RT=2.69 min vi) (5S)-5-(3-{4-[(6-Bromohexyl)oxy]but-1-ynyl}benzyl)-5methylimidazolidine-2,4-dione was prepared using methods similar to those described in Example 5iii LCMS RT=3.39 min vii) (5S)-5-(3-{4-[(6-{[(2R)-2-(2,2-Dimethyl-4H-1,3-benzodioxin-6-yl)-2-hydroxyethyl]amino}hexyl)oxy]but-1-ynyl}benzyl)-5-methylimidazolidine-2,4-dione was prepared using methods similar to those described in Example 5iv LCMS RT=2.63 min viii) (5S)-5-(3-{4-[(6-{[(2R)-2-(2,2-Dimethyl-4H-1,3-benzodioxin-6-yl)-2-hydroxyethyl]amino}hexyl)oxy]butyl}benzyl)-5-methylimidazolidine-2,4-dione was prepared using methods similar to those described in Example 5v LCMS RT=2.65 min ix) (5S)-5-[3-(4-{[6-({(2R)-2-Hydroxy-2-[4-hydroxy-3-(hydroxymethyl)phenyl]ethyl}amino)hexyl]oxy}butyl)benzyl]-5methylimidazolidine-2,4-dione acetate was prepared using methods similar to those described in Example 1xii LCMS RT=2.37 min, ES+ve 542(MH)$^+$.

EXAMPLE 17

2-{3-[3-(4-{[6-({(2R)-2-Hydroxy-2-[4-hydroxy-3-(hydroxymethyl)phenyl]ethyl}amino)hexyl]oxy}butyl)phenyl]-2,4-dioxoimidazolidin-1-yl}acetamide acetate i) 2-[3-(3-Iodophenyl)-2,4-dioxoimidazolidin-1-yl]acetamide A solution of 3-(3-iodophenyl)imidazolidine-2,4-dione (1 g) in DMF (20 ml) was treated with sodium hydride (60% oil dispersion, 158 mg) and 2-bromoacetamide (1.36 g) at 20° C. After 2 h the reaction mixture was treated with aqueous 2M HCl, extracted with EtOAc and dried (MgSO$_4$). The solvent was removed under reduced pressure and the residue was purified by chromatography on Biotage (40 g) eluting with EtOAc to give the title compound (638 mg). LCMS RT=2.32 min.

ii) 2-[3-(3-{4-[(6-Bromohexyl)oxy]but-1-ynyl}phenyl)-2,4-dioxoimidazolidin-1-yl]acetamide was prepared using methods similar to those described in Example 5iii. LCMS RT=3.17 min.

iii) 2-[3-(3-{4-[(6-{[(2R)-2-(2,2-Dimethyl-4H-1,3-benzodioxin-6-yl)-2-hydroxyethyl]amino}hexyl)oxy]but-1-ynyl}phenyl)-2,4-dioxoimidazolidin-1-yl]acetamide was prepared using methods similar to those described in Example 5iv. LCMS RT=2.50 min.

iv) 2-[3-(3-{4-[(6-{[(2R)-2-(2,2-Dimethyl-4H-1,3-benzodioxin-6-yl)-2-hydroxyethyl]amino}hexyl)oxy]butyl}phenyl)-2,4-dioxoimidazolidin-1-yl]acetamide was prepared using methods similar to those described in Example 5v. LCMS RT=2.59 min.

v) 2-{3-[3-(4-{[6-({(2R)-2-Hydroxy-2-[4-hydroxy-3-(hydroxymethyl)phenyl]ethyl}amino)hexyl]oxy}butyl)phenyl]-2,4-dioxoimidazolidin-1-yl]-yl}acetamide acetate was prepared using method similar to those described in Example 1xii. LCMS RT=2.23 min, ES+ve 571 (MH)$^+$.

EXAMPLE 18

5-[4-(4-{[6-({(2)-2-Hydroxy-2-[4-hydroxy-3-(hydroxymethyl)phenyl]ethyl}amino)hexyl]oxy}butyl)benzyl]imidazolidine2,4-dione compound with formic acid (1:1)

i) Methyl N-(aminocarbonyl)-4-iodo-L-phenylalaninate was prepared using methods similar to those described in Example 15iv LCMS RT=2.78 min ii) 5-(4-Iodobenzyl)imidazolidine-2,4-dione was prepared using methods similar to those described in Example 15v LCMS RT=2.54 min iii) 5-{4-[4-({6-[(5R)-5-(2,2-Dimethyl-4H-1,3-benzodioxin-6-yl)-2-oxo-1,3-oxazolidin-3-yl]hexyl}oxy)but-1-ynyl]benzyl}imidazolidine-2,4-dione was prepared using methods similar to those described in Example 3viii LCMS RT=3.22 min iv) 5-{4-[4-({6-[(5R)-5-(2,2-Dimethyl-4H-1,3-benzodioxin-6-yl)-2-oxo-1,3-oxazolidin-3-yl]hexyl}oxy)butyl]benzyl}imidazolidine-2,4-dione was prepared using methods similar to those described in Example 3ix LCMS RT=3.41 min v) 5-[4-(4-{[6-({(2R)-2-Hydroxy-2-[4-hydroxy-3-(hydroxymethyl)phenyl]ethyl}amino)hexyl]oxy}butyl)benzyl]imidazolidine-2,4-dione compound with formic acid (1:1)

was prepared using methods similar to those described in Example 3x

EXAMPLE 19

1-[3-(4-{[6-({(2R)-2-Hydroxy-2-[4-hydroxy-3-(hydroxymethyl)phenyl]ethyl}amino)hexyl]oxy}butyl)phenyl]-1,3-dihydro-2H-imidazol-2-one i) N-(2,2-Dimethoxyethyl)-N'-(3-iodophenyl)urea A suspension of 3-iodophenylisocyanate (1.1 g) in DCM (10 ml) was treated with aminoacetaldehyde dimethyl acetal (0.49 ml) and stirred under nitrogen at 20° C. for 24 h. The reaction mixture was quenched by adding MeOH. The solvents were removed under reduced pressure to give the title compound (1.35 g) LCMS RT=2.92 min.

ii) 1-(3-Iodophenyl)-1,3-dihydro-2H-imidazol-2-one

N(2,2-Dimethoxyethyl)-N'-(3-iodophenyl)urea (618 mg) was dissolved in acetic acid (10 ml) and water (1 ml) and the mixture was stirred at 20° C. for 17 h and then heated to 100° C. for 0.5 h. The solvent was removed under reduced pressure and the residue was dissolved in ethyl acetate. The solution was washed with NaHCO$_3$ solution, dried and purified by chromatography on 10 g silica Bond Elut cartridge eluting with EtOAc-petroleum ether (1:7 to 1:1) to give the title compound (130 mg) LCMS RT=2.66 min.

iii) 1-[3-(4-{[6-({(2R)-2-Hydroxy-2-[4-hydroxy-3-(hydroxymethyl)phenyl]ethyl}amino)hexyl]oxy}butyl)phenyl]-1,3-dihydro-2H-imidazol-2-one may be prepared using for example the methods described in Example 5ii to 5vi. LCMS RT=2.28 min, ES+ve 498 (MH)$^+$.

EXAMPLE 20

3-[3-(4-{[6-({(2R)-2-Hydroxy-2-[4-hydroxy-3-(hydroxymethyl)phenyl]ethyl}amino)hexyl]oxy}butyl)phenyl]-5,5-dimethylimidazolidine-2,4-dione acetate i) 3-(3-Iodophenyl)-5,5-dimethylimidazolidine-2,4-dione BOC-α-methylalanine (1.01 g) and diisopropylethylamine (1.74 ml) in dichloromethane (2 ml) was treated with tetramethylfluoroformamidinium hexafluorophosphate (1.32 g) and the mixture was stirred for 18 h. 3-Iodoaniline (1.09 g) in dichloromethane (2 ml) was added, followed by diisopropylethylamine (1 ml). The mixture was stirred for 84 h and then the solvents were removed under reduced pressure. The residue was partitioned between EtOAc and 2M HCl. The organic solution was washed with 2M HCl, sodium bicarbonate solution, brine and dried (MgSO$_4$). The filtrate was concentrated and then triturated in dichloromethane-cyclohexane (1:1, 20 ml) to give a solid (740 mg). The solution was purified by chromatography on two 10 g silica Bond Elut cartridges eluting with dichloromethane to give additional solid (633 mg). LCMS RT=3.41 min. The solid (735 mg) was dissolved in DMF (3 ml) and then treated with sodium hydride (60% oil dispersion, 109 mg). The mixture was stirred overnight at room temperature and then heated to 75° C. for 3 h. The solvent was removed under reduced pressure and treated with 4M HCl in dioxane. The resulting solution was heated for 2 h at 75° C., concentrated, and the residue was triturated in Et$_2$O to give the title compound (487 mg). LCMS RT=2.79 min ii) 3-(3-{4-[(6-(Bromohexyl)oxy]but-1-ynyl}phenyl)-5,5-dimethylimidazolidine-2,4-dione was prepared using methods similar to those described in Example 5iii. LCMS RT=3.51 min iii) 3-(3-{4-[(6-{[(2R)-2-(2,2-Dimethyl-4H-1,3-benzodioxin-6-yl)-6-yl)-2-hydroxyethyl]amino}hexyl)oxy]but-1-ynyl}phenyl)-5,5-dimethylimidazolidine-2,4-dione was prepared using methods similar to those described in Example 5iv. LCMS RT=2.72 min iv) 3-(3-{4-[(6-{[(2R)-2-(2,2-Dimethyl-4H-1,3-benzodioxin-6-yl)-2-hydroxyethyl]amino}hexyl)oxy]butyl}phenyl)-5,5-dimethylimidazolidine-2,4-dione was prepared using methods similar to those described in Example 5v. LCMS RT=2.60 min v) 3-[3-(4-{[6-({(2R)-2-Hydroxy-2-[4-hydroxy-3-(hydroxymethyl)phenyl]ethyl}amino)hexyl]oxy}butyl)phenyl]-5,5-dimethylimidazolidine-2,4-dione acetate was prepared using methods similar to those described in Example 1xii. LCMS RT=2.47 min, ES+ve 542 (MH)+.

EXAMPLE 21

3-[3-(3-{[7-({(2R)-2-Hydroxy-2-[4-hydroxy-3-(hydroxymethyl)phenyl]ethyl}amino)heptyl]oxy}propyl)phenyl]-1-(methylsulfonyl)imidazolidine-2,4-dione acetate i) 7-[(3-{3-[3-(methylsulfonyl)-2,5-dioxoimidazolidin-1-yl]phenyl}propyl)oxy]heptyl methanesulfonate was prepared using methods similar to those described in Example 1vii. LCMS RT=2.80 min ii) 3-(3-{3-[(7-{[(2R)-2-(2,2-Dimethyl-4H-1,3-benzodioxin-6-yl)-2-hydroxyethyl]amino}heptyl)oxy]propyl}phenyl)-1-(methylsulfonyl)imidazolidine-2,4-dione was prepared using methods similar to those described in Example 1xi. LCMS RT=2.85 min iii) 3-[3-(3-{[7-({(2R)-2-Hydroxy-2-[4-hydroxy-3-(hydroxymethyl)phenyl]ethyl}amino)heptyl]oxy}propyl)phenyl]-1-(methylsulfonyl)imidazolidine-2,4-dione acetate was prepared using methods similar to those described in Example 1xii. LCMS RT=2.54 min, ES+ve 592 (MH)+.

EXAMPLE 22

1-[3-(3-{[6-({(2R)-2-Hydroxy-2-[4-hydroxy-3-(hydroxymethyl)phenyl]ethyl}amino)hexyl]oxy}propyl)phenyl]imidazolidine-2,4-dione acetate i) 1-{3-[3-({6-[(5R)-5-(2,2-Dimethyl-4H-1,3-benzodioxin6-yl)-2-oxo-1,3-oxazolidin-3-yl]hexyl}oxy)prop-1-ynyl]phenyl}imidazolidine-2,4-dione was prepared using methods similar to those described in Example 4ii. LCMS RT=3.43 min ii) 1-{3-[3-({6-[(5R)-5-(2,2-Dimethyl-4H-1,3-benzodioxin-6-yl)-2-oxo-1,3-oxazolidin-3-yl]hexyl}oxy)propyl]phenyl}imidazolidine-2,4-dione was prepared using methods similar to those described in Example 3ix. LCMS RT=3.42 min iii) 1-(3-{3-[(6-{[(2R)-2-(2,2-Dimethyl-4H-1,3-benzodioxin-6-yl)-2-hydroxyethyl]amino{hexyl)oxy]propyl}phenyl)imidazolidine-2,4-dione was prepared using methods similar to those described in Example 3x. LCMS RT=2.60 min iv) 1-[3-(3-{[6-({(2R)-2-Hydroxy-2-[4-hydroxy-3-(hydroxymethyl)phenyl]ethyl}amino)hexyl]oxy}propyl)phenyl]imidazolidine-2,4-dione acetate was prepared using methods similar to those described in Example 1xii. LCMS RT=2.34 min, ES+ve 500 (MH)+

EXAMPLE 23

N-{1-[3-(4-{[6-({(2R)-2-Hydroxy-2-[4-hydroxy-3-(hydroxymethyl)phenyl]ethyl}amino)hexyl]oxy}butyl)benzyl]-2,5-dioxoimidazolidin-4-yl]urea acetate i) N-[1-(3-Iodobenzyl)-2,5-dioxoimidazolidin-4-yl]urea Allantoin (1.58 g) was stirred with meta-iodobenzyl bromide (2.97 g) in DMF (25 ml) at 21° under nitrogen and sodium hydride (60% oil dispersion; 0.40 g) was added over 5 min. After 2 h the solution was partitioned between EtOAc and water and hydrochloric acid was added to give pH 3. The separated aqueous layer was extracted with more EtOAc and the combined organic layers were washed with water and brine twice. After drying (MgSO$_4$), the solution was concentrated to 20 ml. After 1 h the solid was collected by filtration and washed with EtOAc. The residue was boiled with EtOAc (50 ml) and the slurry was allowed to cool. The solid was collected by filtration, washed with ethyl acetate and dried to give the title compound (0.507 g). LCMS RT=2.44 min ii) N-[1-(3-{4-[(6-Bromohexyl)oxy]but-1-ynyl}benzyl)-2,5-dioxoimidazolidin-4-yl]urea was prepared using methods similar to those described in Example 5iii. LCMS RT=3.29 min iii) N-[1-(3-{4-[(6-{[(2R)-2-(2,2-Dimethyl-4H-1,3-benzodioxin-6-yl)-2-hydroxyethyl]amino}hexyl)oxy]but-1-ynyl}benzyl)-2,5-dioxoimidazolidin-4-yl]urea was prepared using methods similar to those described in Example 5iv. LCMS RT=2.57 min iv) N-[1-(3-{4-[(6-{[(2R)-2-(2,2-Dimethyl-4H-1,3-benzodioxin-6-yl)-2-hydroxyethyl]amino}hexyl)oxy]butyl}benzyl)-2,5-dioxoimidazolidin-4-yl]urea was prepared using methods similar to those described in Example 5v. LCMS RT=2.61 min v) N-{1-[3-(4-{[6-({(2R)-2-Hydroxy-2-[4-hydroxy-3-(hydroxymethyl)phenyl]ethyl}amino)hexyl]oxy}butyl)benzyl]-2,5-dioxoimidazolidin-4-yl]urea acetate was prepared using methods similar to those described in Example 1xii. LCMS RT=2.36 min, ES+ve 586 (MH)+

EXAMPLE 24

3-Benzyl-1-[3-(4-{[6-({(2R)-2-hydroxy-2-[4-hydroxy-3-(hydroxymethyl)phenyl]ethyl{amino)hexyl]oxy}butyl)phenyl]imidazolidine-2,4-dione acetate i) 3-Benzyl-1-(3-iodophenyl)imidazolidine-2,4-dione 1-(3-Iodophenyl)imidazolidine-2,4-dione (0.5 g) was taken up in dry DMF (10 ml) and treated with sodium hydride (60% oil dispersion, 73 mg) and stirred for 20 min under nitrogen. Benzyl bromide (0.295 ml) was added and stirring continued for 3 h. 2M HCl (100 ml) was added and the mixture extracted with EtOAc. The combined extracts were washed with saturated aqueous sodium hydrogen carbonate (50 ml), brine (50 ml) and dried (MgSO$_4$). This was recrystallised from MeOH to give the title compound (0.255 g). LCMS RT 3.53 min.

ii) 3-Benzyl-1-(3-{4-[(6-bromohexyl)oxy]but-1-ynyl}phenyl)imidazolidine-2,4-dione was prepared using methods similar to those described in Example 5iii). LCMS RT=3.99 min iii) 3-Benzyl-1-(3-{4-[(6-{[(2R)-2-(2,2-dimethyl-4H-1,3-benzodioxin-6-yl)-2-hydroxyethyl]amino}hexyl)oxy]but-1-ynyl}phenyl)imidazolidine-2,4-dione was prepared using methods similar to those described in Example 5iv). LCMS RT=3.02 min iv) 3-Benzyl-1-(3-{4-[(6-{[(2R)-2-(2,2-dimethyl-4H-1,3-benzodioxin-6-yl)-2-hydroxyethyl]amino}hexyl)oxy]butyl}phenyl)imidazolidine-2,4-dione was prepared using methods similar to those described in Example 5v). LCMS RT=3.08 min v) 3-Benzyl-1-[3-(4-{[6-({(2R)-2-hydroxy-2-[4-hydroxy-3-(hydroxymethyl)phenyl]ethyl}amino)hexyl]oxy}butyl)phenyl]imidazolidine-2,4-dione acetate was prepared using methods similar to those described in Example 1xii). LCMS RT=2.81 min, ES+ve 604 (MH)+.

EXAMPLE 25

1-[3-(4-{[6-({(2R)-2-Hydroxy-2-[4-hydroxy-3-(hydroxymethyl)phenyl]ethyl}amino)hexyl]oxy}butyl)phenyl]-3-methylimidazolidine-2,4-dione acetate i) 1-(3-Iodophenyl)-3-methylimidazolidine-2,4-dione 1-(3-Iodophenyl)imidazolidine-2,4-dione (0.588 g) was suspended in water (13 ml) and treated with potassium hydroxide (0.37 g). The reaction was placed in a warming bath (45° C.) and treated with dimethyl sulfate (0.784 ml). After stirring for 4 h the reaction mixture was chilled and filtered. The cake was washed with water and dried to give the title compound (0.381 g). LCMS RT=2.94 min.

ii) 1-(3-{4-[(6-Bromohexyl)oxy]but-1-ynyl}phenyl)-3-methylimidazolidine-2,4-dione was prepared using methods similar to those described in Example 5iii). LCMS RT=3.64 min.

iii) 1-(3-{4-[(6-{[(2R)-2-(2,2-Dimethyl-4H-1,3-benzodioxin-6-yl)-2-hydroxyethyl]amino}hexyl)oxy]but-1-ynyl}phenyl)-3-methylimidazolidine-2,4-dione was prepared using methods similar to those described in Example 5iv). LCMS RT=2.79 min.

iv) 1-(3-{4-[(6-{[(2R)-2-(2,2-Dimethyl-4H-1,3-benzodioxin-6-yl)-2-hydroxyethyl]amino}hexyl)oxy]butyl}phenyl)-3-methylimidazolidine-2,4-dione was prepared using methods similar to those described in Example 5v). LCMS RT=2.76 min.

v) 1-[3-(4-{[6-({(2R)-2-Hydroxy-2-[4-hydroxy-3-(hydroxymethyl)phenyl]ethyl}amino)hexyl]oxy}butyl)phenyl]-3-methylimidazolidine-2,4-dione acetate was prepared using methods similar to those described in Example 1xii). LCMS RT=2.48 min, ES+ve 527 (MH)+.

EXAMPLE 26

Ethyl {3-[3-(4-{[6-({(2R)-2-hydroxy-2-[4-hydroxy-3-(hydroxymethyl)phenyl]ethyl}amino)hexyl]oxy}butyl)phenyl]-2,5-dioxoimidazolidin-1-yl}acetate acetate i) Ethyl [3-(3-iodophenyl)-2,5-dioxoimidazolidin-1-yl]acetate 1-(3-Iodophenyl)imidazolidine-2,4-dione (0.5 g) was dissolved in dry DMF (10 ml) and treated with sodium hydride (60% oil dispersion, 73 mg) and stirred under nitrogen. After 20 min ethyl chloroacetate (0.255 ml) was added. After 3 h 2M HCl (100 ml) was added and the mixture extracted with EtOAc. The combined extracts were dried (MgSO4) and evaporated under reduced pressure. Trituration with di-tert-butyl ether (2×10 ml) gave the title compound (0.571 g). LCMS RT=3.21 min.

ii) Ethyl [3-(3-{4-[(6-bromohexyl)oxy]but-1-ynyl}phenyl)-2,5-dioxoimidazolidin-1-yl]acetate was prepared using methods similar to those described in Example 5iii). LCMS RT=3.79 min.

iii) Ethyl [3-(3-{4-[(6-{[(2R)-2-(2,2-dimethyl-4H-1,3-benzodioxin-6-yl)-2-hydroxyethyl]amino}hexyl)oxy]but-1-ynyl}phenyl)-2,5-dioxoimidazolidin-1-yl]acetate was prepared using methods similar to those described in Example 5iv). LCMS RT=2.85 min.

iv) Ethyl [3-(3-{4-[(6-{[(2R)-2-(2,2-dimethyl-4H-1,3-benzodioxin-6-yl)-2-hydroxyethyl]amino}hexyl)oxy]butyl}phenyl)-2,5-dioxoimidazolidin-1-yl]acetate was prepared using methods similar to those described in Example 5v). LCMS RT=2.93 min.

v) Ethyl {3-[3-(4-{[6-({(2R)-2-hydroxy-2-[4-hydroxy-3-(hydroxymethyl)phenyl]ethyl}amino)hexyl]oxy}butyl)phenyl]-2,5-dioxoimidazolidin-1-yl}acetate acetate was prepared using methods similar to those described in Example 1xii). LCMS RT=2.65 min, ES+ve 600 (MH)+.

EXAMPLE 27

2-{3-[3-(4-{[6-({(2R)-2-Hydroxy-2-[4-hydroxy-3-(hydroxymethyl)phenyl]ethyl}amino)hexyl]oxy}butyl)phenyl]-2,5-dioxoimidazolidin-1-yl}acetamide acetate i) 2-[3-(3-Iodophenyl)-2,5-dioxoimidazolidin-1-yl]acetamide 1-(3-Iodophenyl)imidazolidine-2,4-dione (0.302 g) was taken up in dry DMF (15 ml) and treated with bromoacetamide (0.399 g) and then with sodium hydride (60% oil dispersion, 48 mg). After 3 h pH 6.4 phosphate buffer (50 ml) was added and the reaction mixture extracted with EtOAc (3×25 ml), dried (MgSO4) and evaporated under reduced pressure. Thee residue was purified by Flash chromatography (Merck 9385, EtOAc then 9:1 EtOAc:MeOH) to give the title compound (0.279 g). LCMS RT=2.62 min.

ii) 2-[3-(3-{4-[(6-Bromohexyl)oxy]but-1-ynyl}phenyl)-2,5-dioxoimidazolidin-1-yl]acetamide was prepared using methods similar to those described in Example 5iii). LCMS RT=3.27 min.

iii) 2-[3-(3-{4-[(6-{[(2R)-2-(2,2-Dimethyl-4H-1,3-benzodioxin-6-yl)-2-hydroxyethyl]amino}hexyl)oxy]but-1-ynyl}phenyl)-2,5-dioxoimidazolidin-1-yl]acetamide was prepared using methods similar to those described in Example 5iv). LCMS RT=2.47 min.

iv) 2-[3-(3-{4-[(6-{[(2R)-2-(2,2-Dimethyl-4H-1,3-benzodioxin-6-yl)-2-hydroxyethyl]amino}hexyl)oxy]butyl}phenyl)-2,5-dioxoimidazolidin-1-yl]acetamide was prepared using methods similar to those described in Example 5v). LCMS RT=2.56 min.

v) 2-{3-[3-(4-{[6-({(2R)-2-Hydroxy-2-[4-hydroxy-3-(hydroxymethyl)phenyl]ethyl}amino)hexyl]oxy}butyl)phenyl]-2,5-dioxoimidazolidin-1-yl}acetamide acetate was prepared using methods similar to those described in Example 1xii). LCMS RT=2.31 min, ES+ve 571 (MH)+.

EXAMPLE 28

1-[3-(4-{[6-({(2R)-2-Hydroxy-2-[4-hydroxy-3-(hydroxymethyl)phenyl]ethyl}amino)hexyl]oxy}butyl)benzyl]imidazolidine-2,4-dione acetate i) Ethyl N-(3-iodobenzyl)glycinate 3-Iodobenzylamine hydrochloride (1.0 g) and diisopropylethylamine (1.29 ml) were taken up in dry dimethylsulfoxide (60 ml) and treated with ethyl bromoacetate and stirred under nitrogen for 2 h. 2M HCl (1.85 ml) and water (250 ml) were added. This was extracted with EtOAc, the aqueous phase was taken to pH 8 and extracted with EtOAc. The combined extracts were dried ($Na_2SO_4$) and concentrated under reduced pressure. The residue was purified by chromatography (Biotage, 40 g) eluting with EtOAc-cyclohexane-diisopropylethylamine (10:89:1 then 20:79:1) to give the title compound (0.571 g) LCMS RT 2.02 min.

ii) 1-(3-Iodobenzyl)imidazolidine-2,4-dione

Ethyl N-(3-iodobenzyl)glycinate (0.567 g) was treated with 1M HCl (3.9 ml) and sodium cyanate (0.345 g) and then refluxed for 30 min. Concentrated HCl (4.5 ml) was added and the reaction mixture refluxed again for 30 min. The reaction mixture was evaporated under reduced pressure and then triturated with EtOAc (3×20 ml). The combined extracts were dried ($Na_2SO_4$) and evaporated under reduced pressure to give the title compound (0.543 g). LCMS RT 2.63 min.

iii) 1-{3-[4-({6-[(5R)-5-(2,2-Dimethyl-4H-1,3-benzodioxin-6-yl)-2-oxo-1,3-oxazolidin-3-yl]hexyl}oxy)but-1-ynyl]benzyl}imidazolidine-2,4-dione was prepared using methods similar to those described in Example 3viii). LCMS RT=3.42 min.

iv) 1-{3-[4-({6-[(5R)-5-(2,2-Dimethyl-4H-1,3-benzodioxin-6-yl)-2-oxo-1,3-oxazolidin-3-yl]hexyl}oxy)butyl]benzyl}imidazolidine-2,4-dione was prepared using methods similar to those described in Example 3ix). LCMS RT=3.4 min.

v) 1-(3-{4-[(6-{[(2R)-2-(2,2-Dimethyl-4H-1,3-benzodioxin6-yl)-2-hydroxyethyl]amino}hexyl)oxy]butyl}benzyl)imidazolidine-2,4-dione was prepared using methods similar to those described in example 3x). LCMS RT=2.6 min.

vi) 1-[3-(4-{[6-({(2R)-2-Hydroxy-2-[4-hydroxy-3-(hydroxymethyl)phenyl]ethyl}amino)hexyl]oxy}butyl)benzyl]imidazolidine-2,4-dione acetate was prepared using methods similar to those described in example 1xii). LCMS RT=2.42 min, ES+ve 528 (MH)$^+$.

EXAMPLE 29

1-Benzyl-3-[3-(4-{[6-({(2R)-2-hydroxy-2-[4-hydroxy-3-(hydroxymethyl)phenyl]ethyl}amino)hexyl]oxy}butyl)phenyl]imidazolidine-2,4-dione acetate i) 1-Benzyl-3-(3-iodophenyl)imidazolidine-2,4-dione A solution of 3-(3-iodophenyl)imidazolidine-2,4-dione (1.7 g) in DMF (20 ml) was treated with sodium hydride (60% oil dispersion, 280 mg) and benzylchloride (1.93 ml) at 20° C. After 2 h the reaction mixture was treated with aqueous 2M HCl, extracted with EtOAc and dried ($MgSO_4$). The solvent was removed under reduced pressure and the residue was purified by chromatography on Biotage (40 g) eluting with petroleum ether-EtOAc (9:1 to 3:2) to give the title compound (1.38 g). LCMS RT=3.27 min.

ii) 3-Benzyl-1-(3-{4-[(6-bromohexyl)oxy]but-1-ynyl}phenyl)imidazolidine-2,4-dione was prepared using methods similar to those described in Example 5iii. LCMS RT=3.90 min.

iii) 1-Benzyl-3-(3-{4-[(6-{[(2R)-2-(2,2-dimethyl-4H-1,3-benzodioxin-6-yl)-2-hydroxyethyl]amino}hexyl)oxy]but-1-ynyl}phenyl)imidazolidine-2,4-dione was prepared using methods similar to those described in Example 5iv. LCMS RT=2.92 min.

iv) 3-Benzyl-1-(3-{4-[(6-{[(2R)-2-(2,2-dimethyl-4H-1,3-benzodioxin-6-yl)-2-hydroxyethyl]amino}hexyl)oxy]butyl}phenyl)imidazolidine-2,4-dione was prepared using methods similar to those described in Example 5v. LCMS RT=2.72 min.

v) 1-Benzyl-3-[3-(4-{[6-({(2R)-2-hydroxy-2-[4-hydroxy-3-(hydroxymethyl)phenyl]ethyl}amino)hexyl]oxy}butyl)phenyl]imidazolidine-2,4-dione acetate was prepared using methods similar to those described in Example 1xii. LCMS RT=2.67 min, ES+ve 604(MH)$^+$.

EXAMPLE 30

3-[3-(4-{[6-({(2R)-2-Hydroxy-2-[4-hydroxy-3-(hydroxymethyl)phenyl]ethyl}amino)hexyl]oxy}butyl)phenyl]-1-(methylsulfonyl)imidazolidine-2,4-dione acetate i) 3-(3-Iodophenyl)-1-(methylsulfonyl)imidazolidine-2,4-dione A solution of 3-(3-iodophenyl)imidazolidine-2,4-dione (950 mg) and N,N-diisopropylethylamine (1.1 ml) in DCM (20 ml) was treated with methanesulfonyl chloride (0.453 ml) at 20° C. After 2 h the reaction mixture was diluted with DCM and washed with aqueous 2M HCl (3×20 ml) and $NaHCO_3$ and dried ($MgSO_4$). The solvent was removed under reduced pressure to give the title compound (1.15 g). LCMS RT=2.91 min.

ii) 3-(3-{4-[(6-Bromohexyl)oxy]but-1-ynyl}phenyl)-1-(methylsulfonyl)imidazolidine-2,4-dione was prepared using methods similar to those described in Example 5iii. LCMS RT=3.60 min.

iii) 3-(3-{4-[(6-{Benzyl[(2R)-2-(2,2-dimethyl-4H-1,3-benzodioxin-4-yl)-2-hydroxyethyl]amino}hexyl)oxy]but-1-ynyl}phenyl-1-(methylsulfonyl)imidazolidine-2,4-dione was prepared using methods similar to those described in Example 6i. LCMS RT=2.94 min.

iv) 3-(3-{4-[(6-{[(2R)-2-(2,2-Dimethyl-4H-1,3-benzodioxin-6-yl)-2-hydroxyethyl]amino}hexyl)oxy]butyl}phenyl)-1-(methylsulfonyl)imidazolidine-2,4-dione was prepared using methods similar to those described in Example 6ii. LCMS RT=2.72 min.

v) 3-[3-(4-{[6-({(2R)-2-Hydroxy-2-[4-hydroxy-3-(hydroxymethyl)phenyl]ethyl}amino)hexyl]oxy}butyl)phenyl]-1-(methylsulfonyl)imidazolidine-24, -dione acetate was prepared using methods similar to those described in Example 1xii. LCMS RT=2.48 min, ES+ve 592(MH)$^+$.

EXAMPLE 31

4-[3-(4-{[6-({(2R)-2-Hydroxy-2-[4-hydroxy-3-(hydroxymethyl)phenyl]ethyl}amino)hexyl]oxy}butyl)phenyl]-1,2,4-triazolidine-3,5-dione acetate i) Ethyl 2-{[(3-iodophenyl)amino]carbonyl}hydrazinecarboxylate A solution of ethyl carbazate (1.25 g) in dichloromethane (20 ml) was treated with 3-iodophenylisocyanate (1.7 g) at 0° C. The reaction mixture was allowed to warm to 20° C. and stirred for 2 h. Ethanol (2 ml) was added and the mixture was stirred for 0.5 h. The solvents were removed under reduced pressure and the residue was triturated in diethyl ether. The white solid was collected by filtration to give the title compound (2.4 g). LCMS RT=2.81 min ii) Ethyl 2-[({3-[4-({6-[(5R)-5-(2,2-dimethyl-4H-1,3-benzodioxin-6-yl)-2-oxo-1,3-oxazolidin-3-yl]hexyl}oxy)but-1-ynyl]phenyl}amino)carbonyl]hydrazinecarboxylate Was prepared using methods similar to those described in Example 3viii LCMS RT=3.46 min iii) Ethyl 2-[({3-[4-({6-[(5R)-5-(2,2-dimethyl-4H-1,3-benzodioxin-6-yl)-2-oxo-1,3-oxazolidin-3-yl]hexyl}oxy)butyl]phenyl}amino)carbonyl]hydrazinecarboxylate Was prepared using methods similar to those described in Example 3ix LCMS RT=3.50 min iv) 4-(3-{4-[(6-{[(2R)-2-(2,2-Dimethyl-4H-1,3-benzodioxin-6-yl)-2-hydroxyethyl]amino}hexyl)oxy]butyl}phenyl)-1,2,4-triazolidine-3,5-dione Was prepared using methods similar to those described in Example 3x LCMS RT=2.42 min v) 4-[3-(4-{[6-({(2R)-2-Hydroxy-2-[4-hydroxy-3-(hydroxymethyl)phenyl]ethyl}amino)hexyl]oxy}butyl)phenyl]-1,2,4-triazolidine-3,5-dione acetate Was prepared using methods similar to those described in Example 1xii LCMS RT=2 min, ES+ve 515 (MH)$^+$

BIOLOGICAL ACTIVITY

The potencies of the aforementioned compounds were determined using frog melanophores transfected with the human beta 2 adrenoreceptor. The cells were incubated with melatonin to induce pigment aggregation. Pigment dispersal was induced by compounds acting on the human beta 2 adrenoreceptor. The beta 2 agonist activity of test compounds was assessed by their ability to induce a change in light transmittance across a melanophore monolayer (a consequence of pigment dispersal). At the human beta 2 adrenoreceptor, compounds of examples 1–31 had $IC_{50}$ values below 1 μM.

Potency at other beta adrenoreceptor subtypes was determined using chinese hamster ovary cells transfected with either the human beta 1 adrenoreceptor or the human beta 3 adrenoreceptor. Agonist activity was assessed by measuring changes in intracellular cyclic AMP.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. A compound of formula (I)

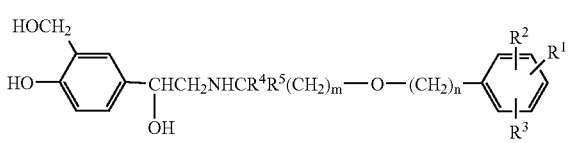

or a salt or solvate thereof, wherein:

m is 5;

n is 4;

$R^1$ is —X—$R^6$; wherein

X is selected from —$(CH_2)_p$— and $C_{2-6}$alkenylene;

$R^6$ is selected from

(a)

(b)

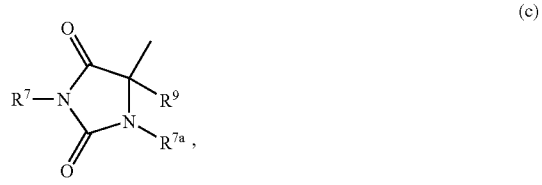
(c)

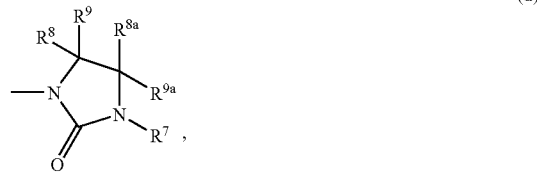
(d)

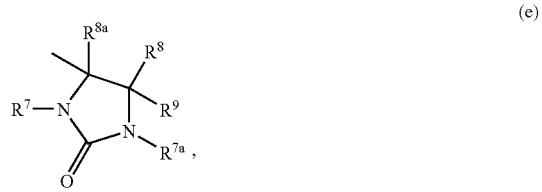
(e)

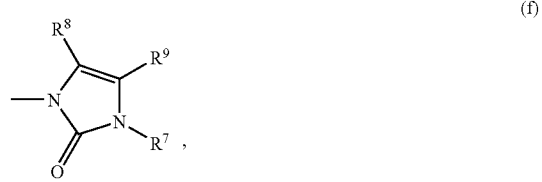
(f)

-continued

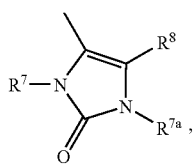
(g)

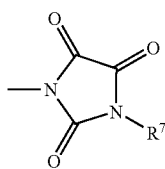
(h)

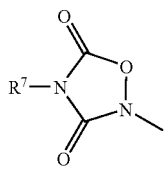
(i)

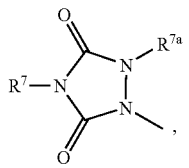
(j)

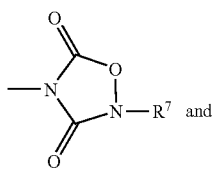
(k)

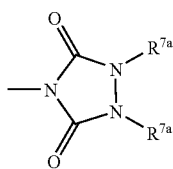
(l)

$R^7$ and $R^{7a}$ are independently selected from hydrogen, $C_{1-6}$alkyl, $C_{3-7}$cycloalkyl, $C(O)R^{7b}$, $C(O)NHR^{7b}$, phenyl, naphthyl, and phenyl($C_{1-4}$alkyl)-, and $R^7$ and $R^{7a}$ are optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$alkyl), —SO$_2$(phenyl), —CO$_2$H, and —CO$_2$($C_{1-4}$alkyl);

$R^{7b}$ is selected from hydrogen, $C_{1-6}$alkyl, $C_{3-7}$cycloalkyl, phenyl, naphthyl, and phenyl($C_{1-4}$alkyl), and $R^{7b}$ is optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$alkyl), —SO$_2$(phenyl), —CO$_2$H, and —CO$_2$($C_{1-4}$alkyl);

$R^8$, $R^{8a}$, $R^9$ and $R^{9a}$ are independently selected from hydrogen, $C_{1-6}$alkyl, $C_{3-7}$cycloalkyl, phenyl, naphthyl, phenyl($C_{1-4}$alkyl)-, —NR$^{10a}$SO$_2$R$^{10}$, —NR$^{10a}$C(O)NR$^{10}$R$^{11}$, —SO$_2$NR$^{10}$R$^{11}$, and $C_{1-6}$alkyl substituted by —CO$_2$R$^{10}$ or —C(O)NR$^{10}$R$^{11}$;

$R^{10}$ $R^{10a}$ and $R^{11}$ are independently selected from hydrogen, $C_{1-6}$alkyl, $C_{3-6}$cycloalkyl, phenyl, and phenyl ($C_{1-4}$ alkyl)-;

p is an integer from 0 to 6;

$R^2$ is selected from hydrogen, $C_{1-6}$alkyl, $C_{1-6}$alkoxy, phenyl, halo, and $C_{1-6}$haloalkyl;

$R^3$ is selected from hydrogen, hydroxyl, $C_{1-6}$alkyl, $C_{1-6}$alkoxy, phenyl, halo, $C_{1-6}$haloalkyl, —NR$^7$CONR$^7$R$^{7a}$, and —SO$_2$NR$^a$R$^b$;

wherein $R^a$ and $R^b$ are independently selected from hydrogen, $C_{1-6}$alkyl, $C_{3-6}$cycloalkyl, phenyl, and phenyl ($C_{1-4}$alkyl), or $R^a$ and $R^b$, together with the nitrogen to which they are bonded, form a 5 membered nitrogen containing ring;

and $R^a$ and $R^b$ are each optionally substituted by one or two groups selected from halo, $C_{1-6}$alkyl, and $C_{1-6}$haloalkyl; and $R^4$ and $R^5$ are independently selected from hydrogen and $C_{1-4}$alkyl with the proviso that the total number of carbon atoms in $R^4$ and $R^5$ is not more than 4.

2. A compound of formula (Ia)

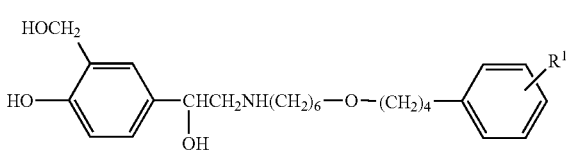
(Ia)

wherein $R^1$ is —X—R$^6$; wherein

X is selected from —(CH$_2$)$_p$- and $C_{2-6}$alkenylene;

$R^6$ is selected from

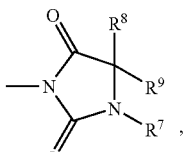
(a)

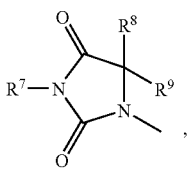
(b)

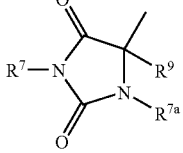
(c)

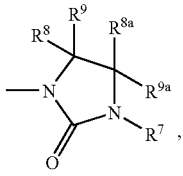
(d)

-continued (e) 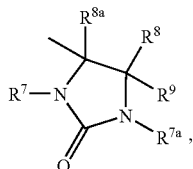

(f) 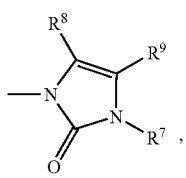

(g) 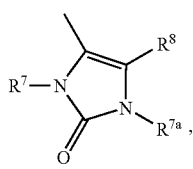

(h) 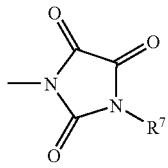

(i) 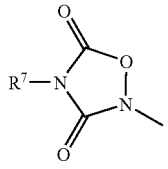

(j) 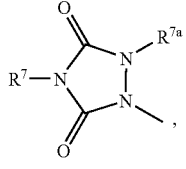

(k) 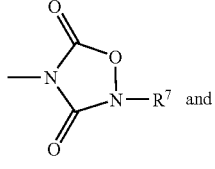

(l) 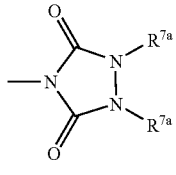

$R^7$ and $R^{7a}$ are independently selected from hydrogen, $C_{1-6}$alkyl, $C_{3-7}$cycloalkyl, $C(O)R^{7b}$, $C(O)NHR^{7b}$, phenyl, naphthyl, and phenyl($C_{1-4}$alkyl)-, and $R^7$ and $R^{7a}$ are optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$alkyl), —SO$_2$(phenyl), —CO$_2$H, and —CO$_2$($C_{1-4}$alkyl);

$R^{7b}$ is selected from hydrogen, $C_{1-6}$alkyl, $C_{3-7}$cycloalkyl, phenyl, naphthyl, and phenyl($C_{1-4}$alkyl), and $R^{7b}$ is optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$alkyl), —SO$_2$(phenyl), —CO$_2$H, and —CO$_2$($C_{1-4}$alkyl);

$R^8$, $R^{8a}$, $R^9$ and $R^{9a}$ are independently selected from hydrogen, $C_{1-6}$alkyl, $C_{3-7}$cycloalkyl, phenyl, naphthyl, phenyl($C_{1-4}$alkyl)-, —NR$^{10a}$SO$_2$R$^{10}$, —NR$^{10a}$C(O)NR$^{10}$R$^{11}$, —SO$_2$NR$^{10}$R$^{11}$, and $C_{1-6}$alkyl substituted by —CO$_2$R$^{10}$ or —C(O)NR$^{10}$R$^{11}$;

$R^{10}$, $R^{10a}$ and $R^{11}$ are independently selected from hydrogen, $C_{1-6}$alkyl, $C_{3-6}$cycloalkyl, phenyl, and phenyl($C_{1-4}$ alkyl)-;

p is an integer from 0 to 6;

or a salt or solvate thereof.

3. A compound of formula (Ib)

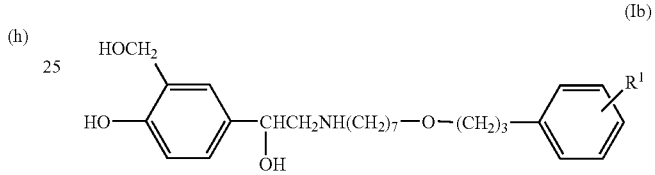

(Ib)

wherein $R^1$
is —X—R$^6$; wherein
X is selected from —(CH$_2$)$_p$- and $C_{2-6}$alkenylene;
$R^6$ is selected from

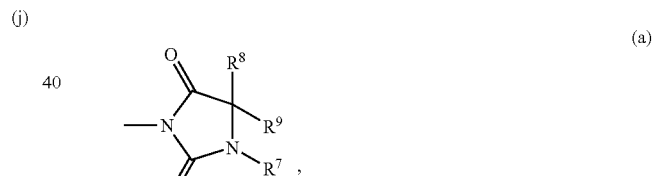 (a)

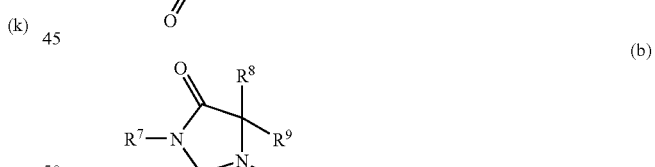 (b)

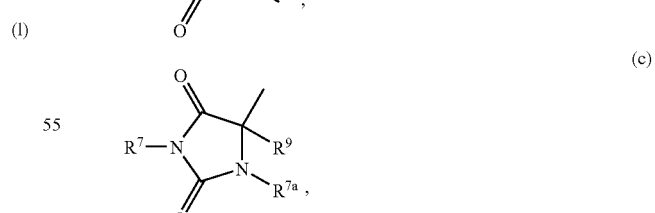 (c)

 (d)

-continued

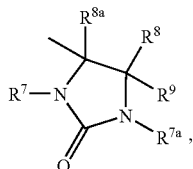
(e)

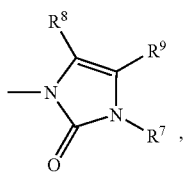
(f)

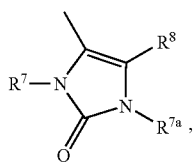
(g)

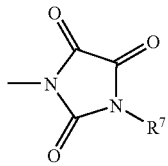
(h)

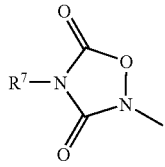
(i)

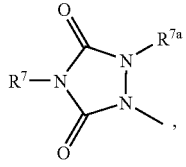
(j)

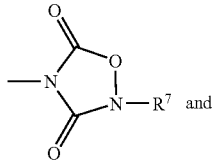
(k)

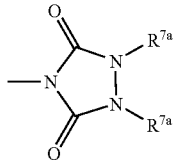
(l)

$R^7$ and $R^{7a}$ are independently selected from hydrogen, $C_{1-6}$alkyl, $C_{3-7}$cycloalkyl, $C(O)R^{7b}$, $C(O)NHR^{7b}$, phenyl, naphthyl, and phenyl($C_{1-4}$alkyl)-, and $R^7$ and $R^{7a}$ are optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$alkyl), —SO$_2$(phenyl), —CO$_2$H, and —CO$_2$($C_{1-4}$alkyl);

$R^{7b}$ is selected from hydrogen, $C_{1-6}$alkyl, $C_{3-7}$cycloalkyl, phenyl, naphthyl, and phenyl($C_{1-4}$alkyl), and $R^{7b}$ is optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$alkyl), —SO$_2$(phenyl), —CO$_2$H, and —CO$_2$($C_{1-4}$alkyl);

$R^8$, $R^{8a}$, $R^9$ and $R^{9a}$ are independently selected from hydrogen, $C_{1-6}$alkyl, $C_{3-7}$cycloalkyl, phenyl, naphthyl, phenyl($C_{1-4}$alkyl)-, —NR$^{10a}$SO$_2$R$^{10}$, —NR$^{10a}$C(O)NR$^{10}$R$^{11}$, —SO$_2$NR$^{10}$R$^{11}$, and $C_{1-6}$alkyl substituted by —CO$_2$R$^{10}$ or —C(O)NR$^{10}$R$^{11}$;

$R^{10}$ $R^{10a}$ and $R^{11}$ are independently selected from hydrogen, $C_{1-6}$alkyl, $C_{3-6}$cycloalkyl, phenyl, and phenyl($C_{1-4}$ alkyl)-;

p is an integer from 0 to 6;

or a salt or solvate thereof.

4. A compound of formula (Ic):

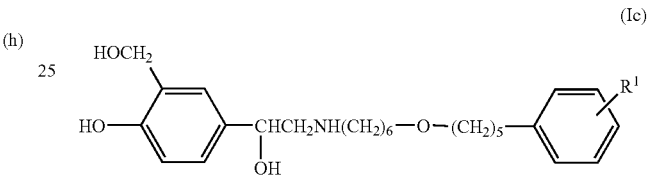
(Ic)

wherein $R^1$
 is —X—$R^6$; wherein
  X is selected from —(CH$_2$)$_p$- and $C_{2-6}$alkenylene;
  $R^6$ is selected from

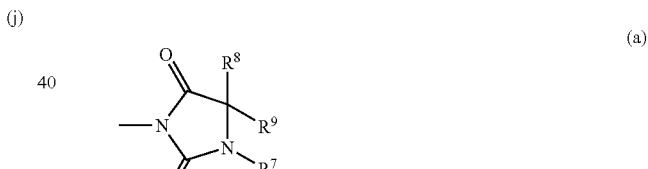
(a)

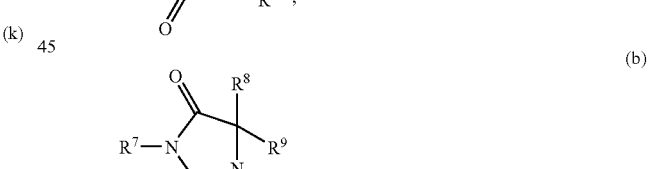
(b)

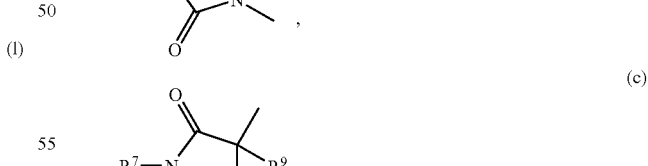
(c)

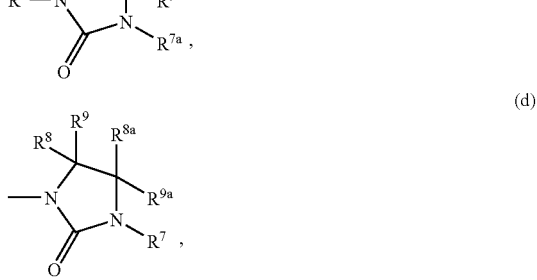
(d)

-continued

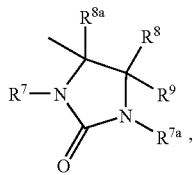 (e)

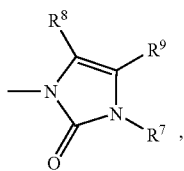 (f)

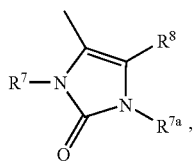 (g)

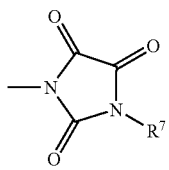 (h)

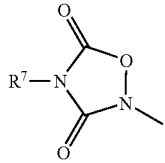 (i)

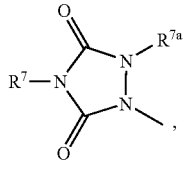 (j)

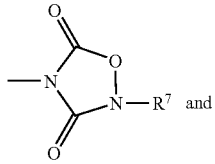 (k)

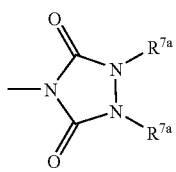 (l)

$R^7$ and $R^{7a}$ are independently selected from hydrogen, $C_{1-6}$alkyl, $C_{3-7}$cycloalkyl, $C(O)R^{7b}$, $C(O)NHR^{7b}$, phenyl, naphthyl, and phenyl($C_{1-4}$alkyl)-, and $R^7$ and $R^{7a}$ are optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$ alkyl), —SO$_2$(phenyl), —CO$_2$H, and —CO$_2$($C_{1-4}$ alkyl);

$R^{7b}$ is selected from hydrogen, $C_{1-6}$alkyl, $C_{3-7}$cycloalkyl, phenyl, naphthyl, and phenyl($C_{1-4}$alkyl), and $R^{7b}$ is optionally substituted by 1 or 2 groups independently selected from halo, $C_{1-6}$alkyl, $C_{1-6}$alkoxy, $C_{1-6}$haloalkyl, —NHC(O)($C_{1-6}$alkyl), —SO$_2$($C_{1-6}$alkyl), —SO$_2$(phenyl), —CO$_2$H, and —CO$_2$($C_{1-4}$alkyl);

$R^8$, $R^{8a}$, $R^9$ and $R^{9a}$ are independently selected from hydrogen, $C_{1-6}$alkyl, $C_{3-7}$cycloalkyl, phenyl, naphthyl, phenyl($C_{1-4}$alkyl)-, —NR$^{10a}$SO$_2$R$^{10}$, —NR$^{10a}$C(O) NR$^{10}$R$^{11}$, —SO$_2$NR$^{10}$R$^{11}$, and $C_{1-6}$alkyl substituted by —CO$_2$R$^{10}$ or —C(O)NR$^{10}$R$^{11}$;

$R^{10}$ $R^{10a}$ and $R^{11}$ are independently selected from hydrogen, $C_{1-6}$alkyl, $C_{3-6}$cycloalkyl, phenyl, and phenyl ($C_{1-4}$ alkyl)-;

p is an integer from 0 to 6;

or a salt or solvate thereof.

5. A compound according to claim 1 or claim 2 selected from:

3-[3-(4-{[6-([(2R)-2-hydroxy-2-[4-hydroxy-3-(hydroxymethyl)phenyl]ethyl}-amino)hexyl]oxy}butyl) phenyl]imidazolidine-2,4-dione;

3-[3-(4-{[6-([(2S)-2-hydroxy-2-[4-hydroxy-3-(hydroxymethyl)phenyl]ethyl}-amino)hexyl]oxy}butyl) phenyl]imidazolidine-2,4-dione;

3-[3-(4-{[6-([(2R/S)-2-hydroxy-2-[4-hydroxy-3-(hydroxymethyl)phenyl]ethyl}-amino)hexyl]oxy}butyl) phenyl]imidazolidine-2,4-dione;

2-{3-[3-(4-{[6-({(2R)-2-Hydroxy-2-[4-hydroxy-3-(hydroxymethyl)phenyl]ethyl}amino)hexyl]oxy}butyl) phenyl]-2,5-dioxoimidazolidin-1-yl}acetamide; and N-{1-[3-(4-{[6-({(2R)-2-Hydroxy-2-[4-hydroxy-3-(hydroxymethyl)phenyl]ethyl}amino)hexyl]oxy}butyl) benzyl]-2,5-dioxoimidazolidin-4-yl}urea;

or a salt or solvate thereof.

6. A compound according to claim 3 or claim 4 which is 3-[3-(5-{[6-({(2R)-2-Hydroxy-2-[4-hydroxy-3-(hydroxymethyl)phenyl]ethyl}amino)hexyl]oxy}pentyl) phenyl]imidazolidine-2,4-dione or a salt or solvate thereof.

7. A compound according to claim 1 wherein $R^6$ is selected from one of the moieties (a)–(j).

8. A method for the treatment of a clinical condition in a mammal, for which a selective $\beta_2$-adrenoreceptor agonist is indicated, wherein said clinical condition is selected from the group consisting of asthma, chronic obstructive pulmonary diseases, respiratory tract infection, and upper respiratory tract disease, said method comprises administrating of a therapeutically effective amount of a compound of formula (I) according to claim 1, or a pharmaceutically acceptable salt or solvate, thereof.

9. A pharmaceutical formulation comprising a compound of formula (I) according to claim 1, or a pharmaceutically acceptable salt or solvate thereof, and a pharmaceutically acceptable carrier or excipient, and optionally one or more other therapeutic ingredients.

10. A process for the preparation of a compound of formula (I), (Ia), (Ib) or (Ic) according to claim 1, or a salt or solvate thereof, wherein said process is selected from the group consisting of (a) through (e):

(a) deprotection a protected intermediate of formula (II):

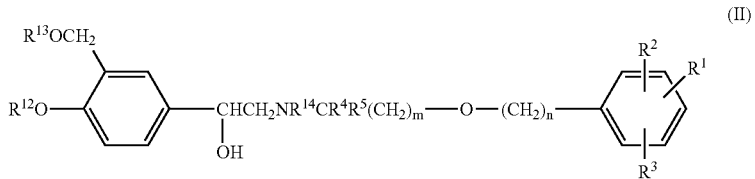

or a salt or solvate thereof, wherein $R^1$, $R^2$, $R^3$, $R^4$, $R^5$, m, and n are as defined for the compound of formula (I) or (Ia), and $R^{12}$, $R^{13}$ and $R^{14}$ are each independently either hydrogen or a protecting group provided that at least one of $R^{12}$, $R^{13}$, and $R^{14}$ is a protecting group;

(b) alkylation an amine of formula (XII)

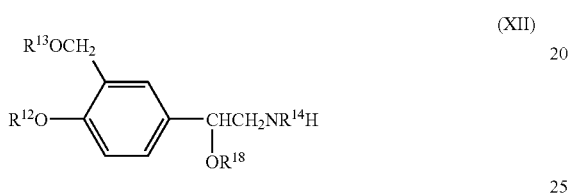

wherein $R^{12}$, $R^{13}$, $R^{14}$ and $R^{18}$ are each independently either hydrogen or a protecting group,
with a compound of formula (XIII):

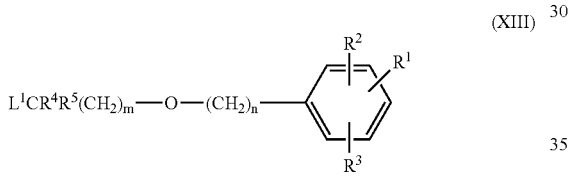

wherein $R^1$, $R^2$, $R^3$, $R^4$, $R^5$, m, and n are as defined for the compound of formula (I) or (Ia) and $L^1$ is a leaving group;

(c) reduction of a compound of formula (XIV):

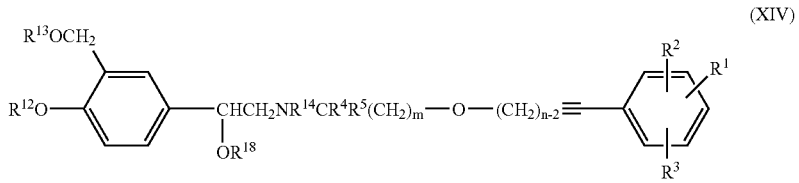

wherein $R^1$, $R^2$, $R^3$, $R^4$, $R^5$, m and n are as defined for formula (I) and $R^{12}$, $R^{13}$, $R^{14}$ and $R^{18}$ each independently represent a hydrogen atom or a protecting group as defined above;

(d) reacting a compound of formula (XVIII):

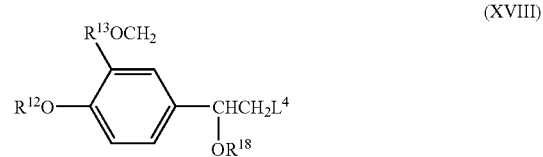

wherein $R^{12}$ $R^{13}$ and $R^{18}$ are as hereinbefore defined and $L^4$ is a leaving group, with an amine of formula (IX):

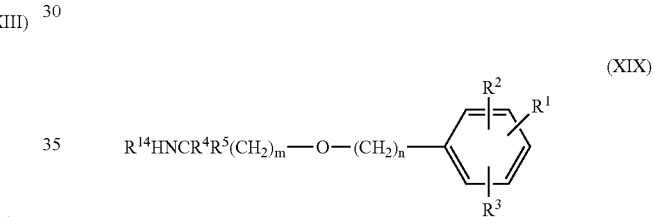

and (e) removal a chiral auxiliary from a compound of formula (IIa):

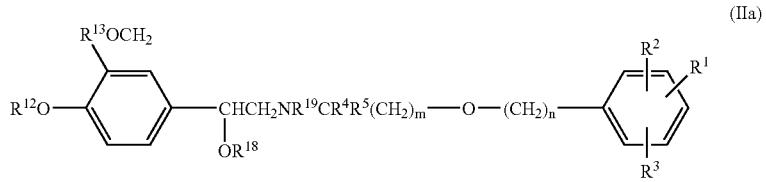

wherein $R^1$, $R^2$, $R^3$, $R^4$, $R^5$, m and n are as defined for formula (I) and $R^{12}$, $R^{13}$, $R^{14}$ and $R^{18}$ each independently represent a hydrogen atom or a protecting group as defined above and $R^{19}$ represents a chiral auxiliary;

wherein any of (a) through (e) may optically be followed by one or more selected from the group consisting of (i) through (iii)

(i) removing any protecting groups;

(ii) separating an enantiomer from a mixture of enantiomers; and (iii) converting the product to a corresponding salt or solvate thereof.

11. A compound of formula (II) as defined in claim 10.

12. A compound of formula (XIV) as defined in claim 10.

13. A method for the treatment of a clinical condition in a mammal, for which a selective $\beta_2$-adrenoreceptor agonist is indicated, wherein said clinical condition is selected from the group consisting of asthma, chronic obstructive pulmonary diseases, respiratory tract infection, and upper respiratory tract disease, said method comprises administering a therapeutically effective amount of a compound of formula (Ia) according to claim 2, or a pharmaceutically acceptable salt or solvate thereof.

14. A pharmaceutical formulation comprising a compound of formula (Ia) according to claim 2, or a pharmaceutically acceptable salt or solvate thereof, and a pharmaceutically acceptable carrier or excipient, and optionally one or more other therapeutic ingredients.

15. A method for the treatment of a clinical condition in a mammal, for which a selective $\beta_2$-adrenoreceptor agonist is indicated, wherein said clincal condition is selected from the group consisting of asthma, chronic obstructive pulmonary diseases, respiratory tract infection, and upper respiratory tract disease, said method comprises administering a therapeutically effective amount of a compound of formula (Ib) according to claim 3, or a pharmaceutically acceptable salt or solvate thereof.

16. A pharmaceutical formulation comprising a compound of formula (Ib) according to claim 3, or a pharmaceutically acceptable salt or solvate thereof, and a pharmaceutically acceptable carrier or excipient, and optionally one or more other therapeutic ingredients.

17. A method for the treatment of a clinical condition in a mammal, for which a selective $\beta_2$-adrenoreceptor agonist is indicated, wherein said clinical condition is selected from the group consisting of asthma, chronic obstructive pulmonary diseases, respiratory tract infection, and upper respiratory tract disease, said method comprises administrating a therapeutically effective amount of a compound of formula (I) according to claim 4, or a pharmaceutically acceptable salt or solvate thereof.

18. A pharmaceutical formulation comprising a compound of formula (Ic) according to claim 4, or a pharmaceutically acceptable salt or solvate thereof, and a pharmaceutically acceptable carrier or excipient, and optionally one or more other therapeutic ingredients.

19. A process according to claim 10, wherein $R^{12}$ and $R^{13}$ together represent a protecting group in the form of a compound of formula (III):

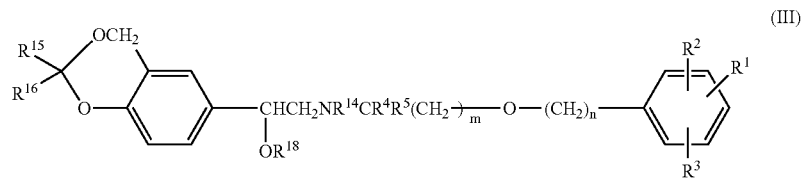

or a salt or solvate thereof, wherein $R^{15}$ and $R^{16}$ are each independently selected from the group consisting of hydrogen, $C_{1-6}$ alkyl, and aryl.

20. A compound of formula (III) as defined in claim 19.

* * * * *

UNITED STATES PATENT AND TRADEMARK OFFICE
CERTIFICATE OF CORRECTION

PATENT NO. : 7,144,908 B2  
APPLICATION NO. : 10/471201  
DATED : December 5, 2006  
INVENTOR(S) : Diane Mary Coe, Michael John Monteith and Panayiotis Alexandrou Procopiou Page 1 of 1

It is certified that error appears in the above-identified patent and that said Letters Patent is hereby corrected as shown below:

In column 66, line 49: (a)-(j), should be: (a)-(l).
In column 70, line 35:

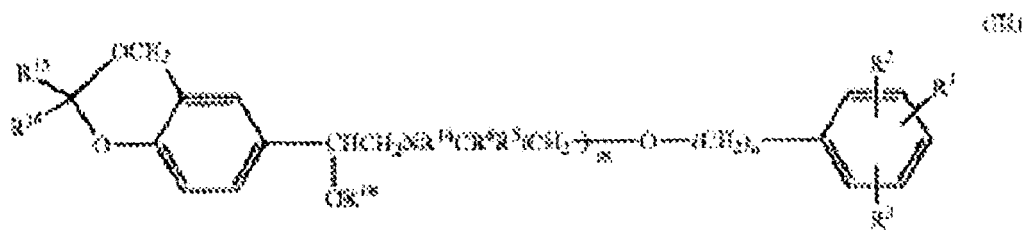

should read:

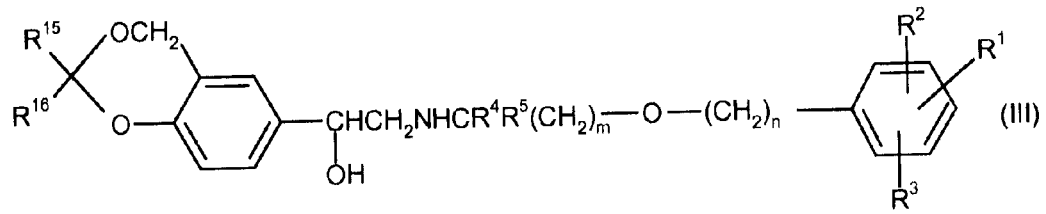

Signed and Sealed this

Seventeenth Day of June, 2008

JON W. DUDAS  
*Director of the United States Patent and Trademark Office*